US011480570B2

(12) United States Patent
Dakappagari et al.

(10) Patent No.: US 11,480,570 B2
(45) Date of Patent: *Oct. 25, 2022

(54) METHOD OF DERIVING A VALUE FOR PERCENT BIOMARKER POSITIVITY FOR SELECTED CELLS PRESENT IN A FIELD OF VIEW

(71) Applicant: Novartis AG, Basel (CH)

(72) Inventors: Naveen Dakappagari, Carlsbad, CA (US); Jennifer Bordeaux, Carlsbad, CA (US); Thai Tran, Carlsbad, CA (US); Ju Young Kim, Carlsbad, CA (US)

(73) Assignee: NOVARTIS AG, Basel (CH)

( * ) Notice: Subject to any disclaimer, the term of this patent is extended or adjusted under 35 U.S.C. 154(b) by 453 days.

This patent is subject to a terminal disclaimer.

(21) Appl. No.: 15/766,307

(22) PCT Filed: Oct. 21, 2016

(86) PCT No.: PCT/US2016/058277
§ 371 (c)(1),
(2) Date: Apr. 5, 2018

(87) PCT Pub. No.: WO2017/070581
PCT Pub. Date: Apr. 27, 2017

(65) Prior Publication Data
US 2019/0293648 A1 Sep. 26, 2019

Related U.S. Application Data

(60) Provisional application No. 62/301,035, filed on Feb. 29, 2016, provisional application No. 62/245,853, filed on Oct. 23, 2015.

(51) Int. Cl.
| | |
|---|---|
| *G01N 33/569* | (2006.01) |
| *G01N 33/574* | (2006.01) |
| *G01N 21/64* | (2006.01) |
| *C12Q 1/6886* | (2018.01) |
| *C12Q 1/6841* | (2018.01) |

(52) U.S. Cl.
CPC ..... *G01N 33/56972* (2013.01); *C12Q 1/6841* (2013.01); *C12Q 1/6886* (2013.01); *G01N 21/6428* (2013.01); *G01N 33/56966* (2013.01); *G01N 33/574* (2013.01); *C12Q 2600/106* (2013.01); *C12Q 2600/158* (2013.01); *G01N 2800/52* (2013.01)

(58) Field of Classification Search
CPC .......... G01N 21/6428; C12Q 2537/143; C12Q 2563/107
See application file for complete search history.

(56) References Cited

U.S. PATENT DOCUMENTS

| | | | | |
|---|---|---|---|---|
| 6,671,624 | B1 * | 12/2003 | Dunlay | B82Y 5/00 |
| | | | | 382/133 |
| 7,565,247 | B1 | 7/2009 | Dunlay et al. | |
| 2007/0020697 | A1 | 1/2007 | Cauling et al. | |
| 2007/0190583 | A1 | 8/2007 | Spector et al. | |
| 2010/0136549 | A1 | 6/2010 | Christiansen et al. | |
| 2010/0267574 | A1 | 10/2010 | You et al. | |
| 2010/0304989 | A1 | 12/2010 | Von Hoff et al. | |
| 2011/0212104 | A1 | 9/2011 | Beaumont et al. | |
| 2012/0014608 | A1 | 1/2012 | Watanabe | |
| 2013/0252876 | A1 * | 9/2013 | Penn | A61F 2/28 |
| | | | | 514/1.1 |
| 2013/0338016 | A1 | 12/2013 | McDonough et al. | |
| 2014/0112955 | A1 | 4/2014 | Bodo et al. | |
| 2014/0369586 | A1 | 12/2014 | Rimm et al. | |
| 2014/0371235 | A1 * | 12/2014 | Wang | C07D 261/04 |
| | | | | 514/254.04 |

FOREIGN PATENT DOCUMENTS

| | | |
|---|---|---|
| JP | 2000-509827 A | 8/2000 |
| JP | 2004-532410 A | 10/2004 |
| JP | 2012-021904 A | 2/2012 |
| WO | WO 2009/138117 A1 | 11/2009 |
| WO | WO 2013/070521 A1 | 5/2013 |
| WO | WO 2013/109944 A1 | 7/2013 |
| WO | WO-2014205184 A2 * | 12/2014 ........... G01N 33/743 |
| WO | WO-2015088930 A1 * | 6/2015 ............... G06T 7/90 |
| WO | WO 2015/100459 A2 | 7/2015 |
| WO | WO 2015/102919 A2 | 7/2015 |
| WO | WO 2015/103037 A2 | 7/2015 |
| WO | WO 2015/124777 A1 | 8/2015 |
| WO | WO 2017/070584 A1 | 4/2017 |

OTHER PUBLICATIONS

Moeder et al., Methods in Molecular Biology, Tumor Biomarker Discovery, vol. 520: 163-175. (Year: 2009).*
How et al., Histochem cell Biol., 2014, 142: 195-204. (Year: 2014).*
Ghaye, "Image Processing on Reconfigurable Hardware for Continuous Monitoring of Fluorescent Biomarkers in Cell Cultures," 184 pages (Jun. 2015).
International Search Report and Written Opinion issued in related International Patent Application No. PCT/US2016/058277, completed Feb. 22, 2017.
Camp et al., "Automated Subcellular Localization and Quantification of Protein Expression in Tissue Microarrays," *Nature Medicine*, vol. 8, No. 11, pp. 1323-1326 (Nov. 2002).
Extended Search Report issued in co-pending European Patent Application No. EP 16858373, dated Feb. 18, 2019.
(Continued)

*Primary Examiner* — Hong Sang
(74) *Attorney, Agent, or Firm* — Foley & Lardner LLP

(57) ABSTRACT

The invention relates, in part, to methods of deriving a value for % biomarker positivity (PBP) for all cells or optionally, one or more subsets thereof, present in a field of view of a tissue sample from a cancer patient. The values for PBP can be indicative of a patient's response to immunotherapy.

18 Claims, 31 Drawing Sheets

(56) References Cited

OTHER PUBLICATIONS

International Preliminary Report on Patentability issued in International Patent Application No. PCT/US2016/058277, dated May 3, 2018.

Office Action issued in co-pending Japanese Patent Application No. 2018-521285, dated Sep. 1, 2020.

Johnson, et al., "Quantitative Spatial Profiling of PD-1/PD-L1 Interaction and HLA-DR/IDO-1 Predicts Improved Outcomes of Anti-PD-1 Therapies in Metastatic Melanoma," Clinical Cancer Research, vol. 24, pp. 21-5250-5260 (2018).

Kluger, et al., "Characterization of PD-L1 Expression and Associated T-cell Infiltrates in Metastatic Melanoma Samples from Variable Anatomic Sites," Clinical Cancer Research, vol. 21, pp. 3052-3060 (2015).

Wimberly, et al., "PD-L1 Expression Correlates with Tumor-Infiltrating Lymphocytes and Response to Neoadjuvant Chemotherapy in Breast Cancer," Cancer Immunology Research, vol. 4, pp. 326-332 (2015).

Yuan et al., "Quantitative Image Analysis of Cellular Heterogeneity in Breast Tumors Complements Genomic Profiling," *Science Translational Medicine*, vol. 4, No. 157, pp. 1-10 (Oct. 2012).

Kerr et al., "Programmed Death-Ligand 1 Immunohistochemistry in Lung Cancer: In What State is this Art?," *Journal of Thoracic Oncology*, vol. 10, No. 7, pp. 985-989 (Jul. 2015).

International Search Report and Written Opinion issued in related International Patent Application No. PCT/US2016/058281, dated Mar. 13, 2017.

Tumeh, et al., "PD-1 Blockade Induces Responses by Inhibiting Adaptive Immune Resistance," *Nature*, vol. 515, No. 7528, pp. 568-571 (2014).

Supplemental European Search Report issued in co-pending European Patent Application No. 16 85 8377 dated Apr. 26, 2019.

International Preliminary Report on Patentability issued in co-pending International Patent Application No. PCT/US2016/058281, dated Mar. 13, 2017.

\* cited by examiner

METHOD OF DERIVING A VALUE FOR PERCENT BIOMARKER POSITIVITY FOR SELECTED CELLS PRESENT IN A FIELD OF VIEW

CROSS-REFERENCE TO RELATED APPLICATIONS

This application is the U.S. National Stage of International Patent Application No. PCT/US2016/058277, filed Oct. 21, 2016, which claims the benefit of priority from U.S. Provisional Patent Application No. 62/245,853, filed Oct. 23, 2015, and U.S. Provisional Patent Application No. 62/301,035, filed Feb. 29, 2016. The contents of these applications are incorporated herein by reference in their entirety.

BACKGROUND

The present invention relates generally to the field of cancer treatment.

SUMMARY

Disclosed herein, in one aspect, are methods of deriving a value for % biomarker positivity (PBP) for all cells or, optionally, one or more subsets thereof present in a field of view, comprising:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a subset biomarker;
(iii) optionally, constructing a third mask of third fluorescence signals representative of all areas present in the field of view, which express a first biomarker of interest;
(iv) combining said first and second masks in a manner that provides a fourth mask comprising fluorescence signals representative of all cells in the field of view, which also express the subset biomarker;
(v) optionally, combining said first and third masks in a manner that provides a fifth mask comprising fluorescence signals representative of all cells in the field of view, which also express the first biomarker of interest;
(vi) deriving a value for PBP for all cells expressing the subset biomarker by dividing the total area of the fourth mask by the total area of the first mask;
(vii) optionally, combining said fourth and fifth masks in a manner that provides a sixth mask comprising fluorescence signals representative of all cells in the field of view, which
(a) express the subset biomarker and the first biomarker of interest; or
(b) express the subset biomarker in the absence of the first biomarker of interest;
and
(viii) optionally, deriving a value for PBP for the first subset of all cells which either (a) express the subset biomarker and the first biomarker of interest or (b) express the subset biomarker in the absence of the first biomarker of interest, by dividing the total area of the sixth mask by the total area of the fourth mask.

In some embodiments, all the recited optional steps are performed. In some embodiments, the method further comprises:
(ix) constructing a seventh mask of fourth fluorescence signals representative of all areas present in the field of view, which express a second biomarker of interest;
(x) combining said first and seventh masks in a manner that provides an eighth mask comprising fluorescence signals representative of a second subset of all cells in the field of view, which also express the second biomarker of interest;
(xi) combining said fourth and eighth masks in a manner that provides a ninth mask comprising fluorescence signals representative of the second subset of all cells in the field of view, which express the subset biomarker and the second biomarker of interest; and
(xii) deriving a value for PBP for the second subset of all cells expressing the subset biomarker and the second biomarker of interest by dividing the total area of the ninth mask by the total area of the fourth mask.

In some embodiments, the method further comprises:
(ix) constructing a seventh mask of fourth fluorescence signals representative of all areas present in the field of view, which express a second biomarker of interest;
(x) subtracting said second mask from said first mask in a manner that provides an eighth mask comprising fluorescence signals representative of all cells that do not express the subset biomarker in the field of view;
(xi) combining said seventh and eighth masks in a manner that provides a ninth mask comprising fluorescence signals representative of all cells that express the second biomarker of interest but do not express the subset biomarker in the field of view; and
(xii) deriving a value for PBP for all cells that express the second biomarker of interest but do not express the subset biomarker by dividing the total area of the ninth mask by the total area of the eighth mask.

In some embodiments, the method further comprises:
(ix) constructing a seventh mask of fourth fluorescence signals representative of all areas present in the field of view, which express a second biomarker of interest
(x) combining said sixth and seventh masks in a manner that provides an eighth mask comprising fluorescence signals representative of all cells that
(a) express the subset biomarker, the first biomarker of interest, and the second biomarker of interest in the field of view;
(b) express the subset biomarker and the first biomarker of interest in the absence of the second biomarker of interest in the field of view; or
(c) express the subset biomarker and the second biomarker of interest in the absence of the first biomarker of interest in the field of view;
and
(xii) deriving a value for PBP for all cells that express the first biomarker of interest or the second biomarker of interest, or a combination thereof, as well as the subset biomarker, by dividing the total area of the eighth mask by the total area of the fourth mask.

In some embodiments, the first biomarker of interest comprises a biomarker selected from CD11b, CD33, HLA-DR, IDO-1, ARG1, granzyme B, B2M, PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the first biomarker of interest comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD4, CD8, FoxP3, CD25, CD16, CD56, CD68, CD163, CD80, and CD86. In some embodiments, the first biomarker of interest comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the first biomarker of interest comprises a biomarker selected from PD-L1, Galectin 9, and MHC. In some embodiments, the second biomarker of interest comprises a biomarker selected from PD-1, TIM-3, and TCR. In some embodiments, the second biomarker of interest is different from the first biomarker of interest and comprises a biomarker selected from CD11b, CD33, HLA-DR, IDO-1, ARG1, granzyme B, B2M, PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the second biomarker of interest is different from the first biomarker of interest and comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the first subset of all the cells in the field of view comprises tumor cells. In some embodiments, the first subset of all the cells in the field of view comprises non-tumor cells. In some embodiments, the first subset of all the cells in the field of view comprises T-cells. In some embodiments, the T-cells express CD3. In some embodiments, the T-cells express CD8. In some embodiments, the T-cells express CD4. In some embodiments the first subset of all the cells in the field of view comprises myeloid cells. In further embodiments the myeloid cells are myeloid derived suppressor cells. In further embodiments the myeloid cells are tumor associated macrophages. In some embodiments, the subset biomarker is expressed only in tumor cells. In some embodiments, the subset biomarker is expressed only in non-tumor cells. In some embodiments, the subset biomarker is expressed in T-cells. In some embodiments, the subset biomarker comprises CD3. In some embodiments, the subset biomarker comprises CD19. In some embodiments, the subset biomarker is expressed in myeloid cells. In some embodiments, the subset biomarker is expressed in myeloid derived suppressor cells. In some embodiments, the subset biomarker is expressed in tumor associated macrophages. In some embodiments, the first biomarker of interest comprises Ki67 and said first subset of all the cells in the field of view comprises CD8 positive cells. In some embodiments, the total area is measured in pixels.

Disclosed herein, in another aspect, are methods of deriving a value for % biomarker positivity (PBP) for all cells or, optionally, one or more subsets thereof present in a field of view, comprising:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a subset biomarker;
(iii) optionally, constructing a third mask of third fluorescence signals representative of all areas present in the field of view, which express a first biomarker of interest;
(iv) combining said first and second masks in a manner that provides a fourth mask comprising fluorescence signals representative of all cells in the field of view, which also express the subset biomarker;
(v) optionally, combining said first and third masks in a manner that provides a fifth mask comprising fluorescence signals representative of a first subset of all cells in the field of view, which also express the first biomarker of interest;
(vi) deriving a value for PBP for all cells expressing the subset biomarker by dividing the total area of the fourth mask by the total area of the first mask;
(vii) optionally, combining said fourth and fifth masks in a manner that provides a sixth mask comprising fluorescence signals representative of the first subset of all cells in the field of view, which express the subset biomarker and the first biomarker of interest; and
(viii) optionally, deriving a value for PBP for the first subset of all cells expressing the subset biomarker and the first biomarker of interest by dividing the total area of the sixth mask by the total area of the fourth mask.

In some embodiments, all the recited optional steps are performed. In some embodiments, the method further comprises:
(ix) constructing a seventh mask of fourth fluorescence signals representative of all areas present in the field of view, which express a second biomarker of interest;
(x) combining said first and seventh masks in a manner that provides an eighth mask comprising fluorescence signals representative of a second subset of all cells in the field of view, which also express the second biomarker of interest;
(xi) combining said fourth and eighth masks in a manner that provides a ninth mask comprising fluorescence signals representative of the second subset of all cells in the field of view, which express the subset biomarker and the second biomarker of interest; and
(xii) deriving a value for PBP for the second subset of all cells expressing the subset biomarker and the second biomarker of interest by dividing the total area of the ninth mask by the total area of the fourth mask.

In some embodiments, the method further comprises:
(ix) constructing a seventh mask of fourth fluorescence signals representative of all areas present in the field of view, which express a second biomarker of interest;
(x) subtracting said second mask from said first mask in a manner that provides an eighth mask comprising fluorescence signals representative of all cells that do not express the subset biomarker in the field of view;
(xi) combining said seventh and eighth masks in a manner that provides a ninth mask comprising fluorescence signals representative of all cells that express the second biomarker of interest but do not express the subset biomarker in the field of view; and
(xii) deriving a value for PBP for all cells that express the second biomarker of interest but do not express the subset biomarker by dividing the total area of the ninth mask by the total area of the eighth mask.

In some embodiments, the first biomarker of interest comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD4, CD8, FoxP3, CD25, CD16, CD56, CD68, CD163, CD80, and CD86. In some embodiments, the first biomarker of interest comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the first biomarker of interest comprises a biomarker selected from PD-L1, Galectin 9, and MHC. In some embodiments, the second biomarker of interest comprises a biomarker selected from PD-1, TIM-3, and TCR. In some embodiments, the second biomarker of interest is different from the first biomarker of interest and comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the first subset of all the cells in the field of view comprises tumor cells. In some embodiments, the first subset of all the cells in the field of view comprises non-tumor cells. In some embodiments, the first subset of all the cells in the field of view comprises T-cells. In some embodiments, the T-cells express CD3. In some embodiments, the T-cells express CD8. In some embodiments, the T-cells express CD4. In some embodiments, the subset biomarker is expressed only in tumor cells. In some embodiments, the subset biomarker is expressed only in non-tumor cells. In some embodiments, the subset biomarker is expressed in T-cells. In some embodiments, the subset biomarker comprises CD3. In some embodiments, the subset biomarker comprises CD19. In some embodiments, the first biomarker of interest comprises Ki67 and said first subset of all the cells in the field of view comprises CD8 positive cells. In some embodiments, the total area is measured in pixels.

In another aspect, disclosed herein are methods monitoring a progress of a patient diagnosed with cancer and undergoing immunotherapy, comprising:
(i) using at least two samples comprising tumor tissue taken from a cancer patient over at least two time points, one prior to and one after initiation of immunotherapy, deriving a value for % biomarker positivity (PBP) for all non-tumor cells expressing a biomarker of interest for each of said at least two samples to obtain at least a first value for PBP and at least a second value for PBP;
(ii) recording said at least first value for PBP and said at least second value for PBP, a change between said at least first value for PBP and said at least second value for PBP being indicative of an effectiveness of said immunotherapy.

In some embodiments, the change is a decrease between said at least first value for PBP and said at least second value for PBP, the decrease being indicative of a positive effectiveness of said immunotherapy. In some embodiments, the change is an increase between said at least first value for PBP and said at least second value for PBP, the increase being indicative of a positive effectiveness of said immunotherapy. In some embodiments, said immunotherapy comprises immune checkpoint therapy.

In another aspect, disclosed herein are methods monitoring a progress of a patient diagnosed with cancer and undergoing immunotherapy, comprising:
(i) using at least two samples comprising tumor tissue taken from a cancer patient over at least two time points, one prior to and one after initiation of immunotherapy, deriving a value for % biomarker positivity (PBP) for all tumor cells expressing a biomarker of interest for each of said at least two samples to obtain at least a first value for PBP and at least a second value for PBP;
(ii) recording said at least first value for PBP and said at least second value for PBP, a change between said at least first value for PBP and said at least second value for PBP being indicative of an effectiveness of said immunotherapy.

In some embodiments, the change is a decrease between said at least first value for PBP and said at least second value for PBP, the decrease being indicative of a positive effectiveness of said immunotherapy. In some embodiments, the change is an increase between said at least first value for PBP and said at least second value for PBP, the increase being indicative of a positive effectiveness of said immunotherapy. In some embodiments, said immunotherapy comprises immune checkpoint therapy.

In another aspect, disclosed herein are methods of deriving a value for % biomarker positivity (PBP) for all tumor cells present in a field of view, comprising:
(i) generating an image of first fluorescence signals representative of nuclei of all cells present in a field of view, and dilating the first fluorescence signals to a diameter of that of an entire cell to construct a first mask of all cells present in the field of view;
(ii) constructing a second mask of second fluorescence signals representative of all areas present in the field of view, which express a tumor biomarker;
(iii) combining said first and second masks in a manner that provides a third mask comprising fluorescence signals representative of all tumor cells in the field of view;
(iv) constructing a fourth mask of third fluorescence signals representative of all areas present in the field of view, which express a biomarker of interest;
(v) combining said third and fourth masks in a manner that provides a fifth mask comprising fluorescence signals representative of all tumor cells in the field of view, which also express the biomarker of interest; and
(vi) deriving a value for PBP for all tumor cells expressing the biomarker of interest by dividing the total area of the fifth mask by the total area of the third mask.

In some embodiments, the biomarker of interest comprises a biomarker selected from the group consisting of PD-L1, Galectin 9, and MHC. In some embodiments, the field of view further comprises non-tumor cells. In some embodiments, the non-tumor cells comprise immune cells and stromal cells. In some embodiments, the total area is measured in pixels.

In another aspect, disclosed herein are methods of deriving a value for % biomarker positivity (PBP) for all non-tumor cells present in a field of view, comprising:
(i) generating an image of first fluorescence signals representative of nuclei of all cells present in a field of view, and dilating the first fluorescence signals to a diameter of that of an entire cell to construct a first mask of all cells present in the field of view;

(ii) constructing a second mask of second fluorescence signals representative of all areas present in the field of view, which express a tumor biomarker;
(iii) subtracting said second mask from said first mask in a manner that provides a third mask comprising fluorescence signals representative of all non-tumor cells in the field of view;
(iv) constructing a fourth mask of fluorescence signals representative of all areas present in the field of view, which express a biomarker of interest;
(v) combining said third and fourth masks in a manner that provides a fifth mask comprising fluorescence signals representative of all non-tumor cells in the field of view, which also express the biomarker of interest; and
(vi) deriving a value for PBP for all non-tumor cells expressing the biomarker of interest by dividing the total area of the fifth mask by the total area of the third mask.

In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the biomarker of interest comprises a biomarker selected from the group consisting of CD11b, CD33, HLA-DR, IDO-1, ARG1, granzyme B, B2M, PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the non-tumor cells comprise immune cells and stromal cells. In some embodiments, the non-tumor cells comprise myeloid cells.

BRIEF DESCRIPTION OF THE DRAWINGS

FIG. 2b shows a non-limiting example of a dilated binary mask of all cells within the image of FIG. 2a.

FIG. 3b shows a non-limiting example of a binary mask of all tumor area within the image of FIG. 3a.

FIG. 3c shows a non-limiting example of a mask of all tumor cells within the image of FIG. 3a.

FIG. 3d shows a non-limiting example of a mask of all non-tumor cells within the image of FIG. 3a.

FIG. 4b shows a non-limiting example of a binary mask of all PD-L1-positive cells within the image of FIG. 4a.

FIG. 4c shows a non-limiting example of a mask of all PD-L1-positive tumor cells within the image of FIG. 4a.

FIG. 4d shows a non-limiting example of a mask of all PD-L1-positive non-tumor cells within the image of FIG. 4a.

FIG. 5b shows a non-limiting example of a binary mask of all PD-1-positive non-tumor cells within the image of FIG. 5a.

FIG. 16b shows a non-limiting example of a dilated binary mask of all cells within the image of FIG. 16a.

FIG. 17b shows a non-limiting example of a binary mask of all PD-1-positive cells within the image of FIG. 17a.

FIG. 18b shows a non-limiting example of a binary mask of all CD3-positive cells within the image of FIG. 18a.

DETAILED DESCRIPTION

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

The term "treating" or "treatment" refers to administering a therapy in an amount, manner, or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the patient.

Figure 32:
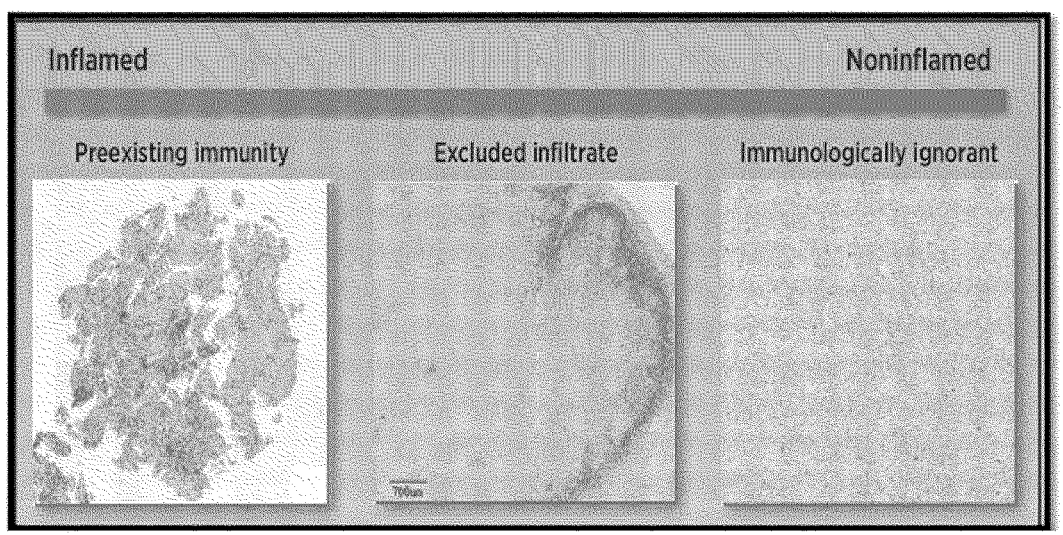
FIG. 32 shows representative tumor classification based on their immune contexture.

Tumors may be classified based on their immune contexture as "hot" (inflamed) or "cold" (non-inflamed) (see FIG. 32). While patients bearing hot tumors may be expected to respond to certain immunotherapies and potentially live longer than patients bearing cold tumors, it has been previously unclear to those skilled in the art as to which biomarkers correlate with response and survival.

To address this issue, some embodiments of the methods described herein aid in the identification of cancer patients who respond to one or more immunotherapies via expression of immune exhaustion biomarkers (e.g., PD-1 and PD-L1) and cancer patients who do not respond (i.e., non-responders) via the presence of cell types known to cause immune suppression (e.g., CD11b, HLA-DR, IDO-1, ARG1) or highly proliferating tumor cells devoid of MHC class I expression (e.g., Ki67+, B2M−). In some embodiments, the methods described herein comprise use of multiplex immunohistochemistry assays (e.g., multiplex FIHC assays) based on specific immune suppression or activation signatures. Non-limiting examples of multiplex FIHC assays based on specific immune suppression or activation signatures are shown in the following table.

| Objective | Multiplex FIHC Assay |
|---|---|
| T Cell Suppression | CD3 + PD-1 + PD-L1 |
| | Tumor marker (CK or S100) + PD-1 + PD-L1 |
| | CD3 + LAG3 + TIM3 |
| | CD3 + CD25 + FOXP3 |
| | CTLA-4 + CD80 |

| Objective | Multiplex FIHC Assay |
|---|---|
| Myeloid Suppression | CD11b + HLA-DR(−) IDO-1 (TAM) |
| | CD11b + HLA-DR (+) ARG1 (fMDSC) |
| T Cell Activation | CD3 + CD8 + Ki67 |
| | CD3 + CD8 + Granzyme B |
| Immune cell | CD3 + CD4 + CD8 |
| Enumeration | Tumor marker (CK or S100) + CD16 + CD56 |
| | Tumor marker (CK or S100) + CD68 + CD163 |
| Identification of | Tumor marker (CK or S100) + |
| cold tumors | CD3 (−) B2M (−) Ki67 (+) |

In one aspect, provided herein are methods of deriving a value for % biomarker positivity (PBP) for all cells or, optionally, one or more subsets thereof, present in a field of view of a tissue sample taken from a cancer patient.

In some embodiments, the sample may be stained using a plurality of fluorescence tags with affinity for specific biomarkers. A digital image of the stained sample may be obtained, and the image further analyzed based on the location of the fluorescence tags. Rather than whole-image analysis, fields of view may be prioritized based on the number of cells that express a first biomarker of interest. A predetermined number of fields of view may then be further analyzed for fluorescence signals. In some embodiments, the use of four different types of fluorescence tags generates an image of fluorescence signals corresponding to a first biomarker of interest and an image of fluorescence signals corresponding a second biomarker of interest as well as to an image of fluorescence signals corresponding a biomarker expressed by all cells and an image of fluorescence signals corresponding a subset biomarker (e.g., a biomarker expressed by tumor cells). In further embodiments, the images of fluorescence signals are manipulated to generate one or more masks of fluorescence signals corresponding to cells within the image. In some embodiments, the one or more masks of fluorescence signals comprise one or more selected from the group consisting of a mask of all cells within the image, a mask of all cells that express the subset biomarker (e.g., all tumor cells) within the image, a mask of all cells that do not express the subset biomarker (e.g., all non-tumor cells) within the image, a mask of all cells expressing a first biomarker of interest within the image, and a mask of all cells expressing a second biomarker of interest within the image. The areas of these masks may be used to derive a value for PBP as desired. In some embodiments, a value for PBP for all cells expressing the subset biomarker is derived. In some embodiments, a value for PBP for a first subset of all cells expressing the subset biomarker and the first biomarker of interest is derived. In some embodiments, a value for PBP for a second subset of all cells expressing the subset biomarker and the second biomarker of interest is derived. In some embodiments, a value for PBP for a second subset of all cells that express the second biomarker of interest but do not express the subset biomarker is derived.

Accordingly, in some embodiments, provided herein are methods of deriving a value for % biomarker positivity (PBP) for all cells or, optionally, one or more subsets thereof present in a field of view, comprising:
  (i) generating an image of first fluorescence signals representative of nuclei of all cells present in a field of view, and dilating the first fluorescence signals to a diameter of that of an entire cell to construct a first mask of all cells present in the field of view;
  (ii) constructing a second mask of second fluorescence signals representative of all areas present in the field of view, which express a subset biomarker;
  (iii) optionally, constructing a third mask of third fluorescence signals representative of all areas present in the field of view, which express a first biomarker of interest;
  (iv) combining said first and second masks in a manner that provides a fourth mask comprising fluorescence signals representative of all cells in the field of view, which also express the subset biomarker;
  (v) optionally, combining said first and third masks in a manner that provides a fifth mask comprising fluorescence signals representative of all cells in the field of view, which also express the first biomarker of interest;
  (vi) deriving a value for PBP for all cells expressing the subset biomarker by dividing the total area of the fourth mask by the total area of the first mask;
  (vii) optionally, combining said fourth and fifth masks in a manner that provides a sixth mask comprising fluorescence signals representative of all cells in the field of view, which
    (a) express the subset biomarker and the first biomarker of interest; or
    (b) express the subset biomarker in the absence of the first biomarker of interest;
    and
  (viii) optionally, deriving a value for PBP for the first subset of all cells which either (a) express the subset biomarker and the first biomarker of interest or (b) express the subset biomarker in the absence of the first biomarker of interest, by dividing the total area of the sixth mask by the total area of the fourth mask.

In some embodiments, the optional steps are not performed. In some embodiments, the total area is measured in pixels. In some embodiments, the total area of the fourth mask and the total area of the first mask are each measured in pixels. In some embodiments, the total area of the sixth mask and the total area of the fourth mask are each measured in pixels. In some embodiments, the total area of the first mask, the total area of the fourth mask, and the total area of the sixth mask are each measured in pixels. In some embodiments, a pixel is 0.5 µm wide.

In some embodiments, provided herein are methods of deriving a value for % biomarker positivity (PBP) for all cells or, optionally, one or more subsets thereof present in a field of view, comprising:
  (i) generating an image of first fluorescence signals representative of nuclei of all cells present in a field of view, and dilating the first fluorescence signals to a diameter of that of an entire cell to construct a first mask of all cells present in the field of view;
  (ii) constructing a second mask of second fluorescence signals representative of all areas present in the field of view, which express a subset biomarker;
  (iii) optionally, constructing a third mask of third fluorescence signals representative of all areas present in the field of view, which express a first biomarker of interest;
  (iv) combining said first and second masks in a manner that provides a fourth mask comprising fluorescence signals representative of all cells in the field of view, which also express the subset biomarker;
  (v) optionally, combining said first and third masks in a manner that provides a fifth mask comprising fluorescence signals representative of all cells in the field of view, which also express the first biomarker of interest;
  (vi) deriving a value for PBP for all cells expressing the subset biomarker by dividing the total area of the fourth mask by the total area of the first mask;

(vii) optionally, combining said fourth and fifth masks in a manner that provides a sixth mask comprising fluorescence signals representative of all cells in the field of view, which express the subset biomarker and the first biomarker of interest; and (viii) optionally, deriving a value for PBP for the first subset of all cells expressing the subset biomarker and the first biomarker of interest by dividing the total area of the sixth mask by the total area of the fourth mask.

In some embodiments, the optional steps are not performed.
In some embodiments, the total area is measured in pixels.
In some embodiments, the total area of the fourth mask and the total area of the first mask are each measured in pixels.
In some embodiments, the total area of the sixth mask and the total area of the fourth mask are each measured in pixels.
In some embodiments, the total area of the first mask, the total area of the fourth mask, and the total area of the sixth mask are each measured in pixels. In some embodiments, a pixel is 0.5 µm wide.

In some embodiments, provided herein are methods of deriving a value for % biomarker positivity (PBP) for all cells or, optionally, one or more subsets thereof present in a field of view, comprising:

(i) generating an image of first fluorescence signals representative of nuclei of all cells present in a field of view, and dilating the first fluorescence signals to a diameter of that of an entire cell to construct a first mask of all cells present in the field of view;

(ii) constructing a second mask of second fluorescence signals representative of all areas present in the field of view, which express a subset biomarker;

(iii) constructing a third mask of third fluorescence signals representative of all areas present in the field of view, which express a first biomarker of interest;

(iv) combining said first and second masks in a manner that provides a fourth mask comprising fluorescence signals representative of all cells in the field of view, which also express the subset biomarker;

(v) combining said first and third masks in a manner that provides a fifth mask comprising fluorescence signals representative of a first subset of all cells in the field of view, which also express the first biomarker of interest;

(vi) deriving a value for PBP for all cells expressing the subset biomarker by dividing the total area of the fourth mask by the total area of the first mask;

(vii) combining said fourth and fifth masks in a manner that provides a sixth mask comprising fluorescence signals representative of the first subset of all cells in the field of view, which express the subset biomarker and the first biomarker of interest; and (viii) deriving a value for PBP for the first subset of all cells expressing the subset biomarker and the first biomarker of interest by dividing the total area of the sixth mask by the total area of the fourth mask.

In some embodiments, the total area is measured in pixels.
In some embodiments, the total area of the fourth mask and the total area of the first mask are each measured in pixels.
In some embodiments, the total area of the sixth mask and the total area of the fourth mask are each measured in pixels.
In some embodiments, the total area of the first mask, the total area of the fourth mask, and the total area of the sixth mask are each measured in pixels. In some embodiments, a pixel is 0.5 µm wide.

In some embodiments, the method further comprises:
(ix) constructing a seventh mask of fourth fluorescence signals representative of all areas present in the field of view, which express a second biomarker of interest;

(x) combining said first and seventh masks in a manner that provides an eighth mask comprising fluorescence signals representative of a second subset of all cells in the field of view, which also express the second biomarker of interest;

(xi) combining said fourth and eighth masks in a manner that provides a ninth mask comprising fluorescence signals representative of the second subset of all cells in the field of view, which express the subset biomarker and the second biomarker of interest; and (xii) deriving a value for PBP for the second subset of all cells expressing the subset biomarker and the second biomarker of interest by dividing the total area of the ninth mask by the total area of the fourth mask.

In some embodiments, the total area is measured in pixels.
In some embodiments, the total area of the ninth mask and the total area of the fourth mask are each measured in pixels.
In some embodiments, a pixel is 0.5 µm wide.

In some embodiments, the method further comprises:
(ix) constructing a seventh mask of fourth fluorescence signals representative of all areas present in the field of view, which express a second biomarker of interest;

(x) subtracting said second mask from said first mask in a manner that provides an eighth mask comprising fluorescence signals representative of all cells that do not express the subset biomarker in the field of view;

(xi) combining said seventh and eighth masks in a manner that provides a ninth mask comprising fluorescence signals representative of all cells that express the second biomarker of interest but do not express the subset biomarker in the field of view; and (xii) deriving a value for PBP for all cells that express the second biomarker of interest but do not express the subset biomarker by dividing the total area of the ninth mask by the total area of the eighth mask.

In some embodiments, the method further comprises:
(ix) constructing a seventh mask of fourth fluorescence signals representative of all areas present in the field of view, which express a second biomarker of interest;

(x) combining said sixth and seventh masks in a manner that provides an eighth mask comprising fluorescence signals representative of all cells that
  (a) express the subset biomarker, the first biomarker of interest, and the second biomarker of interest in the field of view;
  (b) express the subset biomarker and the first biomarker of interest in the absence of the second biomarker of interest in the field of view; or
  (c) express the subset biomarker and the second biomarker of interest in the absence of the first biomarker of interest in the field of view;
and
(xii) deriving a value for PBP for all cells that express the first biomarker of interest or the second biomarker of interest, or a combination thereof, as well as the subset biomarker, by dividing the total area of the eighth mask by the total area of the fourth mask.

In some embodiments, the method further comprises additional cycles of steps analogous to steps (ix), (x), and (xii) with respect to one or more additional biomarkers of interest (e.g., a third biomarker of interest).

In some embodiments, the total area is measured in pixels.
In some embodiments, the total area of the ninth mask and the total area of the eighth mask are each measured in pixels.
In some embodiments, a pixel is 0.5 µm wide.

In some embodiments, a subset of cells identified by a subset biomarker and a non-subset of cells corresponds to tumor cells and non-tumor cells, respectively or vice versa. In some embodiments, a subset of cells identified by a subset biomarker and a non-subset of cells corresponds to viable cells and non-viable cells, respectively or vice versa. In some embodiments, a subset of cells identified by a subset biomarker is a subset of viable cells and a non-subset of cells consists of the viable cells not included in the subset of viable cells. In some embodiments, a subset of cells identified by a subset biomarker and a non-subset of cells corresponds to T cells and non-T cells, respectively or vice versa. In some embodiments, a subset of cells identified by a subset biomarker and a non-subset of cells corresponds to myeloid cells and non-myeloid cells, respectively or vice versa.

In some embodiments, the first subset of all the cells in the field of view comprises tumor cells. In some embodiments, the first subset of all the cells in the field of view comprises non-tumor cells. In some embodiments, the first subset of all the cells in the field of view comprises non-tumor and tumor cells.

In some embodiments, the first subset of all the cells in the field of view comprises T-cells. In some embodiments, the T-cells express CD3. In some embodiments, the T-cells express CD8. In some embodiments, the T-cells express CD4.

In some embodiments, the first biomarker of interest comprises a biomarker selected from the group consisting of CD11b, CD33, HLA-DR, IDO-1, ARG1, granzyme B, B2M, PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the first biomarker of interest comprises a biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, ICOS, CD28, CD4, CD8, FoxP3, CD25, CD16, CD56, CD68, CD163, CD80, and CD86. In some embodiments, the first biomarker of interest comprises a biomarker selected from the group consisting of PD-L1, PD-L2, B7-H3, B7-H4, HLA-DR, Galectin 9, CD80, CD86, 4.1BBL, ICOSL, CD40, OX40L, IDO-1, and GITRL. In some embodiments, the first biomarker of interest comprises a biomarker selected from the group consisting of PD-L1, Galectin 9, and MHC In some embodiments, the first biomarker of interest comprises PD-L1.

In some embodiments, the second biomarker of interest comprises a biomarker selected from PD-1, TIM-3, and TCR. In some embodiments, the second biomarker of interest comprises PD-1.

In some embodiments, the first biomarker of interest and the second biomarker of interest are different from each other and comprise a biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, ICOS, CD28, CD3, CD4, CD8, FoxP3, CD25, CD16, CD56, CD68, CD163, CD80, and CD86. In some embodiments, the first biomarker of interest and the second biomarker of interest are different from each other and comprise a biomarker selected from the group consisting of CD11b, CD33, HLA-DR, IDO-1, ARG1, granzyme B, B2M, PD-L1, PD-L2, B7-H3, B7-H4, HLA-DR, Galectin 9, CD80, CD86, 4.1BBL, ICOSL, CD40, OX40L, IDO-1, GITRL, ICOS, CD28, CD3, CD4, CD8, FoxP3, CD25, CD16, CD56, CD68, CD163, CD80, and CD86.

In some embodiments, the first biomarker of interest comprises a biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, ICOS, CD28, CD4, CD8, FoxP3, CD25, CD16, CD56, CD68, CD163, CD80, and CD86; and the second biomarker of interest comprises a biomarker selected from PD-1, TIM-3, and TCR. In some embodiments, the first biomarker of interest comprises PD-L1 and the second biomarker of interest comprises PD-1. In some embodiments, the first biomarker of interest comprises PD-L1 and the second biomarker of interest comprises CD80. In some embodiments, the first biomarker of interest comprises CTLA-4 and the second biomarker of interest comprises CD80. In some embodiments, the first biomarker of interest comprises PD-L2 and the second biomarker of interest comprises PD-1. In some embodiments, the first biomarker of interest comprises CTLA-4 and the second biomarker of interest comprises CD86. In some embodiments, the first biomarker of interest comprises LAG-3 and the second biomarker of interest comprises HLA-DR. In some embodiments, the first biomarker of interest comprises TIM-3 and the second biomarker of interest comprises Galectin 9. In some embodiments, the first biomarker of interest comprises 41BB and the second biomarker of interest comprises 4.1BBL. In some embodiments, the first biomarker of interest comprises OX40 and the second biomarker of interest comprises OX40L. In some embodiments, the first biomarker of interest comprises CD40 and the second biomarker of interest comprises CD40L. In some embodiments, the first biomarker of interest comprises ICOS and the second biomarker of interest comprises ICOSL. In some embodiments, the first biomarker of interest comprises GITR and the second biomarker of interest comprises GITRL. In some embodiments, the first biomarker of interest comprises HLA-DR and the second biomarker of interest comprises TCR. In some embodiments, the first biomarker of interest comprises CD25 and the second biomarker of interest comprises FoxP3. In some embodiments, the first biomarker of interest comprises CD4 and the second biomarker of interest comprises CD8. In some embodiments, the first biomarker of interest comprises CD3 and the second biomarker of interest comprises PD-1. In some embodiments, the first biomarker of interest comprises CD56 and the second biomarker of interest comprises CD16. In some embodiments, the first biomarker of interest comprises HLA-DR and the second biomarker of interest comprises IDO-1. In some embodiments, the first biomarker of interest comprises CD33 and the second biomarker of interest comprises ARG1.

In some embodiments, the subset biomarker is only expressed in tumor cells. In some embodiments, the subset biomarker is expressed only in non-tumor cells. In some embodiments, the subset biomarker is expressed in T-cells. In some embodiments, the subset biomarker comprises CD3. In some embodiments, the subset biomarker comprises CD19. In some embodiments, the subset biomarker comprises CD45. In some embodiments, the subset biomarker is expressed in myeloid cells. In some embodiments, the subset biomarker comprises CD11b.

In some embodiments, the first biomarker of interest comprises Ki67 and the first subset of all the cells in the field of view comprises CD8 positive cells.

In some embodiments, the fluorescence signals are from four fluorescence tags, each specific to a different biomarker. In further embodiments, a first fluorescence tag is associated with the first biomarker of interest, a second fluorescence tag is associated with the second biomarker of interest, a third fluorescence tag is associated with a third biomarker of interest, and a fourth fluorescence tag is associated with a fourth biomarker of interest. In some embodiments, the first biomarker of interest comprises a tumor and non-tumor marker. In some embodiments, the second biomarker of interest comprises a non-tumor marker. In some embodiments, the first biomarker of interest comprises a tumor and non-tumor marker, and the second biomarker of interest comprises a non-tumor marker. In some embodiments, the third biomarker of interest is expressed by all cells. In some embodiments, the fourth biomarker of interest is expressed only in tumor cells. In some embodiments, the third biomarker of interest is expressed by all cells and the fourth biomarker of interest is expressed only in tumor cells. In some embodiments, the fourth biomarker of interest is the subset biomarker. In some embodiments, the third biomarker of interest is expressed by all cells and the fourth biomarker of interest is the subset biomarker. In some embodiments, one or more fluorescence tags comprise a fluorophore conjugated to an antibody having a binding affinity for a specific biomarker or another antibody. In some embodiments, one or more fluorescence tags are fluorophores with affinity for a specific biomarker.

Examples of fluorophores include, but are not limited to, fluorescein, 6-FAM, rhodamine, Texas Red, California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight® 350, DyLight® 405, DyLight® 488, DyLight® 549, DyLight® 594, DyLight® 633, DyLight® 649, DyLight® 680, DyLight® 750, DyLight® 800, phycoerythrin, PerCP (peridinin chlorophyll-a Protein), PerCP-Cy5.5, JOE (6-carboxy-4', 5'-dichloro-2', 7'-dimethoxyfluorescein), NED, ROX (5-(and -6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br2, BODIPY® 530/550, BODIPY® 558/568, BODIPY® 630/650, BODIPY® 650/665, BODIPY® R6G, BODIPY® TMR, BODIPY® TR, OPAL™ 520, OPAL™ 540, OPAL™ 570, OPAL™ 620, OPAL™ 650, OPAL™ 690, and combinations thereof. In some embodiments, the fluorophore is selected from the group consisting of DAPI, Cy® 2, Cy® 3, Cy® 3,5, Cy® 5, Cy® 7, FITC, TRITC, a 488 dye, a 555 dye, a 594 dye, Texas Red, and Coumarin. Examples of a 488 dye include, but are not limited to, Alexa Fluor® 488, OPAL™ 520, DyLight® 488, and CF™ 488A. Examples of a 555 dye include, but are not limited to, Alexa Fluor® 555. Examples of a 594 dye include, but are not limited to, Alexa Fluor® 594.

As used herein, a "field of view" refers to a section of a whole-slide digital image of a tissue sample. In some embodiments, the whole-slide image has 2-200 predetermined fields of view. In some embodiments, the whole-slide image has 10-200 predetermined fields of view. In some embodiments, the whole-slide image has 30-200 predetermined fields of view. In some embodiments, the whole-slide image has 10-150 predetermined fields of view. In some embodiments, the whole-slide image has 10-100 predetermined fields of view. In some embodiments, the whole-slide image has 10-50 predetermined fields of view. In some embodiments, the whole-slide image has 10-40 predetermined fields of view. In some embodiments, the whole-slide image has 10, 15, 20, 25, 30, 35, 40, 45, 50, 55, 60, 65, 70, 75, 80, 85, 90, 95, or 100, including increments therein, predetermined fields of view.

In methods disclosed herein, the cancer patient is a mammal. In some embodiments, the mammal is human. In some embodiments, the mammal is not human. In further embodiments, the mammal is mouse, rat, guinea pig, dog, cat, or horse.

In methods disclosed herein, tumor tissue is taken from a cancer patient. The type of cancer includes, but is not limited to, cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues including connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites, or a combination of one or more thereof.

Examples of immunotherapy include, but are not limited to, monoclonal antibodies (e.g., alemtuzumab or trastuzumab), conjugated monoclonal antibodies (e.g., ibritumomab tiuxetan, brentuximab vendotin, or ado-trastuzumab emtansine), bispecific monoclonal antibodies (blinatumomab), immune checkpoint inhibitors (e.g., ipilimumab, pembrolizumab, nivolumab, atezolizumab, or durvalumab), thalidomide, lenalidomide, pomalidomide, and imiquimod, and combinations thereof. In some embodiments, the immunotherapy comprises immune checkpoint therapy.

In another aspect, provided herein are methods of deriving a value for % biomarker positivity (PBP) for all tumor cells present in a field of view, comprising:
  (i) generating an image of first fluorescence signals representative of nuclei of all cells present in a field of view, and dilating the first fluorescence signals to a diameter of that of an entire cell to construct a first mask of all cells present in the field of view;
  (ii) constructing a second mask of second fluorescence signals representative of all areas present in the field of view, which express a tumor biomarker;
  (iii) combining said first and second masks in a manner that provides a third mask comprising fluorescence signals representative of all tumor cells in the field of view;
  (iv) constructing a fourth mask of third fluorescence signals representative of all areas present in the field of view, which express a biomarker of interest;
  (v) combining said third and fourth masks in a manner that provides a fifth mask comprising fluorescence signals representative of all tumor cells in the field of view, which also express the biomarker of interest; and
  (vi) deriving a value for PBP for all tumor cells expressing the biomarker of interest by dividing the total area of the fifth mask by the total area of the third mask.

In some embodiments, the total area is measured in pixels. In some embodiments, the total area of the fifth mask and the total area of the third mask are each measured in pixels. In some embodiments, a pixel is 0.5 μm wide. In some embodiments, the biomarker of interest comprises a biomarker selected from the group consisting of PD-L1, Galectin 9, and MHC. In some embodiments, the biomarker of interest comprises PD-L1. In some embodiments, the biomarker of interest comprises Galectin 9. In some embodiments, the biomarker of interest comprises MHC. In some embodiments, the field of view further comprises non-tumor cells. In some embodiments, the non-tumor cells comprise immune cells and stromal cells.

In another aspect, provided herein are methods of deriving a value for % biomarker positivity (PBP) for all non-tumor cells present in a field of view, comprising:
  (i) generating an image of first fluorescence signals representative of nuclei of all cells present in a field of view, and dilating the first fluorescence signals to a diameter of that of an entire cell to construct a first mask of all cells present in the field of view;
  (ii) constructing a second mask of second fluorescence signals representative of all areas present in the field of view, which express a tumor biomarker;
  (iii) subtracting said second mask from said first mask in a manner that provides a third mask comprising fluorescence signals representative of all non-tumor cells in the field of view;
  (iv) constructing a fourth mask of fluorescence signals representative of all areas present in the field of view, which express a biomarker of interest;
  (v) combining said third and fourth masks in a manner that provides a fifth mask comprising fluorescence signals representative of all non-tumor cells in the field of view, which also express the biomarker of interest; and
  (vi) deriving a value for PBP for all non-tumor cells expressing the biomarker of interest by dividing the total area of the fifth mask by the total area of the third mask.

In some embodiments, the total area is measured in pixels. In some embodiments, the total area of the fifth mask and the total area of the third mask are each measured in pixels. In some embodiments, a pixel is 0.5 μm wide. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, and CD28. In some embodiments, the biomarker of interest comprises PD-L1. In some embodiments, the biomarker of interest comprises PD-1. In some embodiments, the non-tumor cells comprise immune cells and stromal cells.

In another aspect, disclosed herein are methods monitoring a progress of a patient diagnosed with cancer and undergoing immunotherapy, comprising:
(i) using at least two samples comprising tumor tissue taken from a cancer patient over at least two time points, one prior to and one after initiation of immunotherapy, deriving a value for % biomarker positivity (PBP) for all non-tumor cells expressing a biomarker of interest for each of said at least two samples to obtain at least a first value for PBP and at least a second value for PBP;
(ii) recording said at least first value for PBP and said at least second value for PBP, a change between said at least first value for PBP and said at least second value for PBP being indicative of an effectiveness of said immunotherapy.

In some embodiments, the change is a decrease between said at least first value for PBP and said at least second value for PBP, the decrease being indicative of a positive effectiveness of said immunotherapy. In some embodiments, the change is an increase between said at least first value for PBP and said at least second value for PBP, the increase being indicative of a positive effectiveness of said immunotherapy. In some embodiments, the immunotherapy comprises immune checkpoint therapy. In some embodiments, the biomarker of interest comprises a biomarker selected from the group consisting of CD11b, CD33, HLA-DR, IDO-1, ARG1, granzyme B, B2M, PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, ICOS, CD28, CD4, CD8, FoxP3, CD25, CD16, CD56, CD68, CD163, CD80, CD86, PD-1, TIM-3, and TCR. In some embodiments, the biomarker of interest comprises a biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, ICOS, CD28, PD-1, TIM-3, and TCR. In some embodiments, the biomarker of interest comprises PD-L1. In some embodiments, the biomarker of interest comprises PD-1.

In another aspect, disclosed herein are methods monitoring a progress of a patient diagnosed with cancer and undergoing immunotherapy, comprising:
(i) using at least two samples comprising tumor tissue taken from a cancer patient over at least two time points, one prior to and one after initiation of immunotherapy, deriving a value for % biomarker positivity (PBP) for all tumor cells expressing a biomarker of interest for each of said at least two samples to obtain at least a first value for PBP and at least a second value for PBP;
(ii) recording said at least first value for PBP and said at least second value for PBP, a change between said at least first value for PBP and said at least second value for PBP being indicative of an effectiveness of said immunotherapy.

In some embodiments, the change is a decrease between said at least first value for PBP and said at least second value for PBP, the decrease being indicative of a positive effectiveness of said immunotherapy. In some embodiments, the change is an increase between said at least first value for PBP and said at least second value for PBP, the increase being indicative of a positive effectiveness of said immunotherapy. In some embodiments, the biomarker of interest comprises a biomarker selected from the group consisting of PD-L1, Galectin 9, and MHC. In some embodiments, the biomarker of interest comprises PD-L1. In some embodiments, the biomarker of interest comprises Galectin 9. In some embodiments, the biomarker of interest comprises MHC. In some embodiments, the immunotherapy comprises immune checkpoint therapy.

In another aspect, disclosed herein are methods monitoring immune cell modulation of a patient diagnosed with cancer and undergoing immunotherapy, comprising:
(i) using at least two samples comprising tumor tissue taken from a cancer patient over at least two time points, one prior to and one after initiation of immunotherapy, deriving a value for % biomarker positivity (PBP) for all non-tumor cells expressing a biomarker of interest for each of said at least two samples to obtain at least a first value for PBP and at least a second value for PBP;
(ii) recording said at least first value for PBP and said at least second value for PBP, a change between said at least first value for PBP and said at least second value for PBP being indicative of an effectiveness of said immunotherapy.

In some embodiments, the change is a decrease between said at least first value for PBP and said at least second value for PBP, the decrease being indicative of a positive effectiveness of said immunotherapy. In some embodiments, the change is an increase between said at least first value for PBP and said at least second value for PBP, the increase being indicative of a positive effectiveness of said immunotherapy. In some embodiments, the immunotherapy comprises immune checkpoint therapy. In some embodiments, the biomarker of interest comprises a biomarker selected from the group consisting of CD11b, CD33, HLA-DR, IDO-1, ARG1, granzyme B, B2M, PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86. In some embodiments, the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, ICOS, CD28, CD4, CD8, FoxP3, CD25, CD16, CD56, CD68, CD163, CD80, CD86, PD-1, TIM-3, and TCR. In some embodiments, the biomarker of interest comprises a biomarker selected from the group consisting of PD-L1, PD-L2, B7-H3, B7-H4, HLA-DR, Galectin 9, CD80, CD86, 4.1BBL, ICOSL, CD40, OX40L, IDO-1, GITRL, ICOS, CD28, PD-1, TIM-3, and TCR. In some embodiments, the biomarker of interest comprises PD-L1. In some embodiments, the biomarker of interest comprises PD-1.

In another aspect, disclosed herein are methods of treating cancer in a patient in need thereof, the method comprising (i) deriving a first value for % biomarker positivity (PBP) for all tumor cells or all non-tumor cells present in a field of view according to a method described herein; (ii) recording the first value for PBP; (iii) administering at least a first dose of immunotherapy to the patient; (iv) deriving a second value for PBP for all tumor cells or all non-tumor cells present in a field of view according to a method described herein after the administration of the at least first dose; (v) recording the second value for PBP; (vi) calculating the change between the first value for PBP and the second value for PBP; and (vii) adjusting the subsequent dose of immunotherapy that is administered to the patient. In some embodiments, adjusting the subsequent dose comprises one or more actions selected from the group consisting of increasing the dose of immunotherapy, decreasing the dose of immunotherapy; increasing a time period between doses of immunotherapy; decreasing the time period between doses of immunotherapy; replacing the immunotherapy with another immunotherapy; replacing the immunotherapy with non-immunotherapy; and terminating immunotherapy.

In another aspect, disclosed herein are methods of treating cancer in a patient in need thereof, the method comprising (i) deriving a first value for % biomarker positivity (PBP) for all tumor cells or all non-tumor cells present in a field of view according to a method described herein; (ii) recording the first value for PBP; (iii) administering at least a first dose of immunotherapy to the patient as part of a dosing regimen; (iv) deriving a second value for PBP for all tumor cells or all non-tumor cells present in a field of view according to a method described herein after the administration of the at least first dose; (v) recording the second value for PBP; (vi) calculating the change between the first value for PBP and the second value for PBP; and (vii) administering a subsequent dose of the immunotherapy without an alteration to the dosing regimen.

Figure 11:
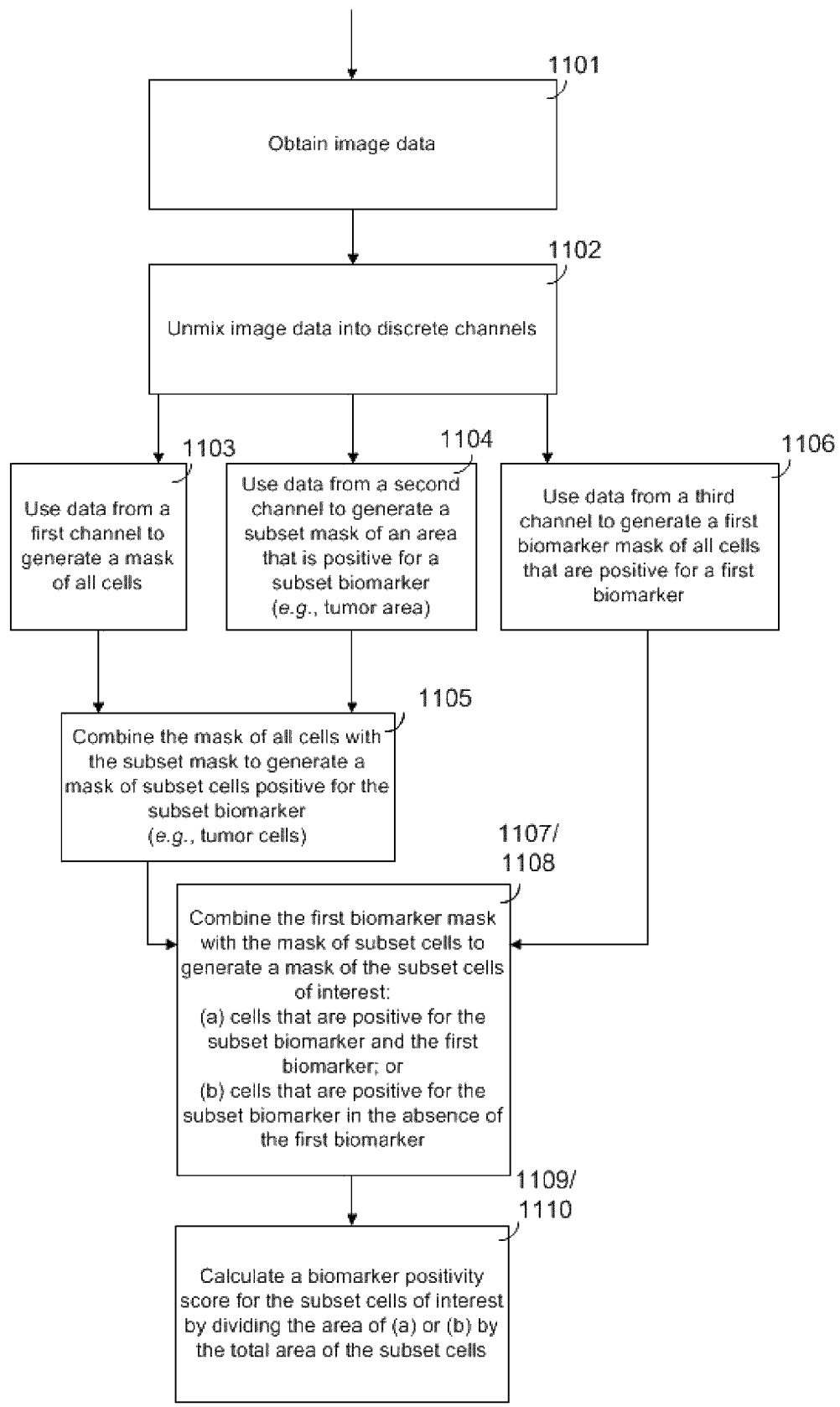
FIG. 11 is a flowchart of a process for deriving a value of biomarker positivity, according to an exemplary embodiment.

FIG. 11 is a flowchart depicting the steps of one embodiment of a method for deriving a value for % biomarker positivity (PBP). In step 1101, image data is obtained and in step 1102, the image data is unmixed such that data specific to various types of fluorescence signals are separated into different channels. In step 1103, data from a first channel is used to generate a mask of all cells. In step 1104, data from a second channel is used to generate a mask of the area in a field of view that expresses a subset biomarker, for example, this subset mask may be a mask of a tumor area present in a field of view. In step 1105, the all cell mask and the subset mask (e.g., a tumor area mask) are combined to generate a mask of all subset cells.

In some embodiments, a subset of cells identified by a subset biomarker and a non-subset of cells corresponds to tumor cells and non-tumor cells, respectively or vice versa. In some embodiments, a subset of cells identified by a subset biomarker and a non-subset of cells corresponds to viable cells and non-viable cells, respectively or vice versa. In some embodiments, a subset of cells identified by a subset biomarker is a subset of viable cells and a non-subset of cells consists of the viable cells not included in the subset of viable cells. In some embodiments, a subset of cells identified by a subset biomarker and a non-subset of cells corresponds to T cells and non-T cells, respectively or vice versa. In some embodiments, a subset of cells identified by a subset biomarker and a non-subset of cells corresponds to myeloid cells and non-myeloid cells, respectively or vice versa.

In certain embodiments, combining the all cell mask and the subset mask may identify all tumor cells and/or all non-tumor cells. The process may be carried out on only a selected type of cell of interest, for example, only tumor cells or only non-tumor cells. The process may also be directed to an analysis of both. In step 1106, data from a third channel is used to generate a mask of all cells that are positive for a biomarker (based on fluorescence signals representing the presence of a fluorescent tag with an affinity for binding to the particular biomarker of interest). In steps 1107 and 1108, the biomarker mask generated in step 1106 is combined with the subset cell mask generated in step 1105. Step 1107 combines the biomarker mask with the subset cell mask in a first manner, to generate a mask of all subset cells that are positive for the biomarker. Step 1108 combines the biomarker mask with the subset cell mask in a second manner, to generate a mask of subset cells that are not positive for the biomarker. One or both of steps 1107 and 1108 may be performed according the various embodiments of the method. In step 1109/1110, a PBP score is calculated by dividing the area of the subset cells of interest (e.g., the subset cells that are positive for the biomarker identified by the mask in step 1107 or the subset cells that are not positive for the biomarker identified by the mask in step 1108) by the total area of all subset cells. One or both of steps 1109 and 1110 may be performed according the various embodiments of the method.

Figure 12:
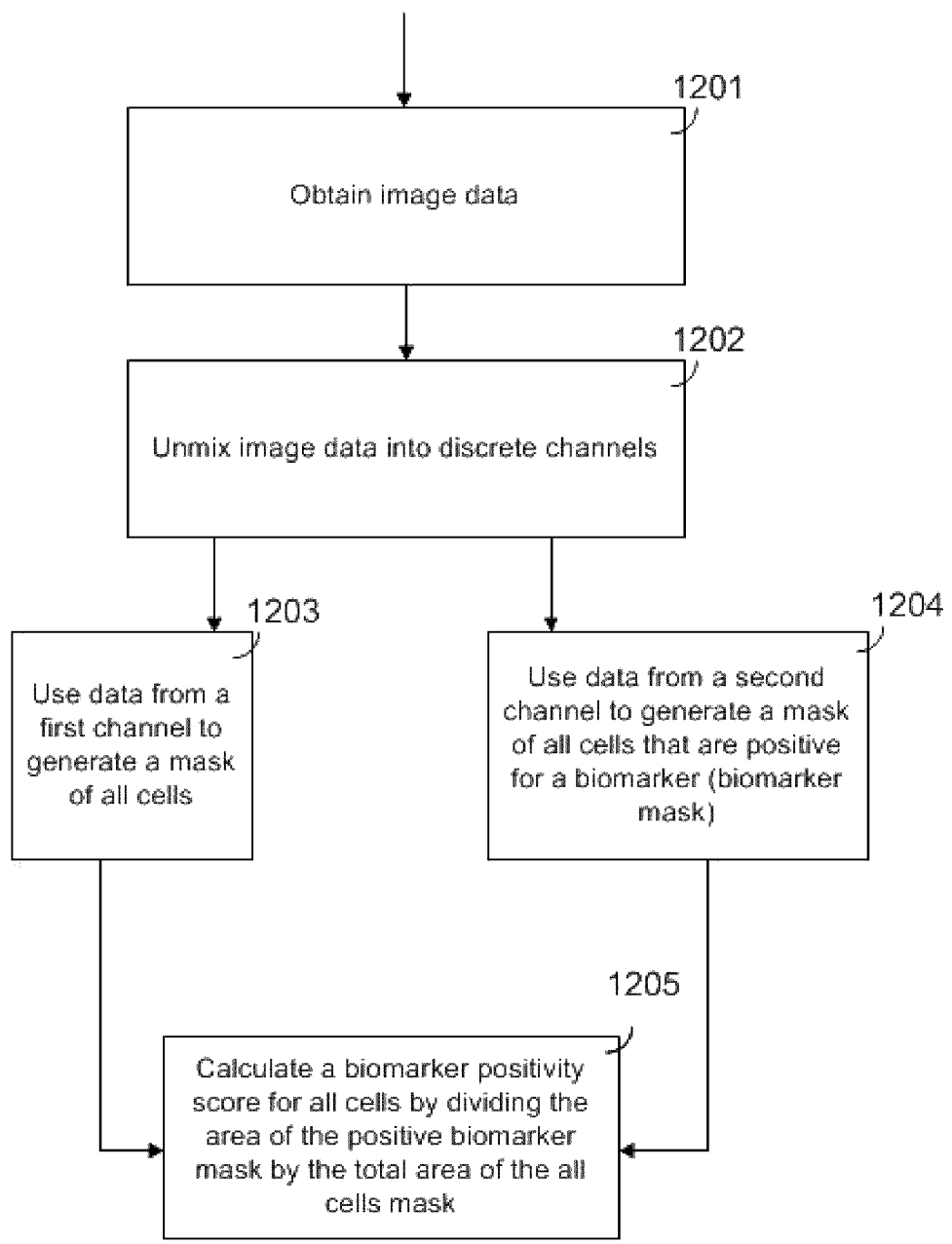
FIG. 12 is a flowchart of a process for deriving a value of biomarker positivity, according to a second exemplary embodiment.

FIG. 12 is a flowchart depicting the steps of a second embodiment of a method for deriving a value for % biomarker positivity (PBP). In step 1201, image data is obtained and in step 1202, the image data is unmixed such that data specific to various types of fluorescence signals are separated into different channels. In step 1203, data from a first channel is used to generate a mask of all cells. In step 1204, data from a second channel is used to generate a mask of all cells that are positive for a biomarker (based on fluorescence signals representing the presence of a fluorescent tag with an affinity for binding to the particular biomarker of interest). In step 1205, a PBP score is calculated by dividing the area of the cells that are positive for the biomarker (which is identified by the mask created in step 1204) by the total area of all cells of interest (from step 1203). The process of FIG. 12 may be carried out separately or concurrently with the method depicted in FIG. 11. In other words, a PBP score may be calculated for all cells, all tumor cells, and all non-tumor cells, or any combination thereof, may combining the methods of FIGS. 11 and 12.

Figure 13:
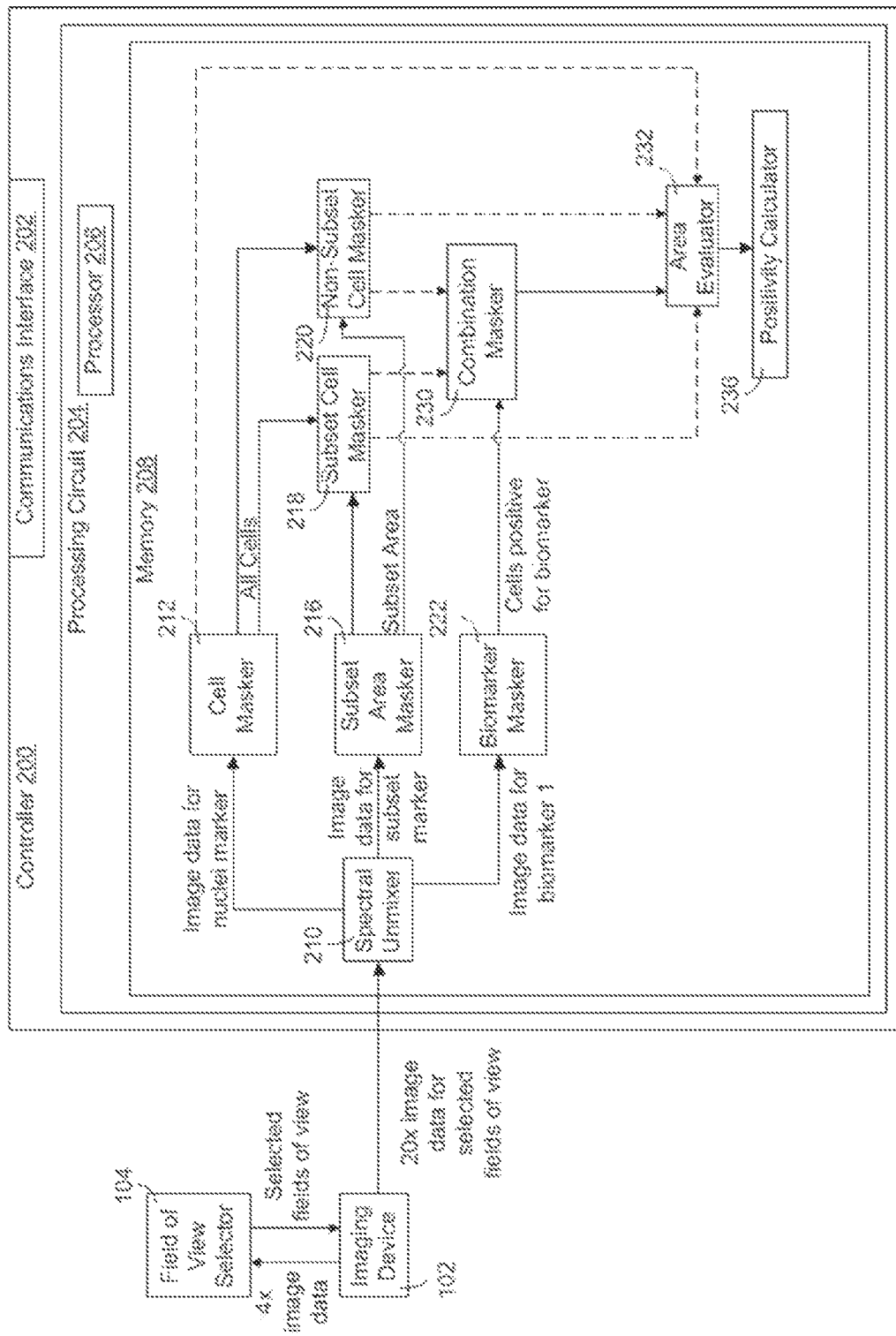
FIG. 13 is a block diagram of a controller configured to derive a value of biomarker positivity, according to an exemplary embodiment.

In the methods disclosed herein, the manipulation of the digital images may be carried out by a computing system comprising a controller, such as the controller illustrated in the block diagram of FIG. 13, according to an exemplary embodiment. Controller 200 is shown to include a communications interface 202 and a processing circuit 204. Communications interface 202 may include wired or wireless interfaces (e.g., jacks, antennas, transmitters, receivers, transceivers, wire terminals, etc.) for conducting data communications with various systems, devices, or networks. For example, communications interface 202 may include an Ethernet card and port for sending and receiving data via an Ethernet-based communications network and/or a WiFi transceiver for communicating via a wireless communications network. Communications interface 202 may be configured to communicate via local area networks or wide area networks (e.g., the Internet, a building WAN, etc.) and may use a variety of communications protocols (e.g., BACnet, IP, LON, etc.).

Communications interface 202 may be a network interface configured to facilitate electronic data communications between controller 200 and various external systems or devices (e.g., imaging device 102). For example, controller 200 may receive imaging data for the selected fields of view from the imaging device 102, to analyze the data and calculate the spatial proximity score (SPS).

Still referring to FIG. 13, processing circuit 204 is shown to include a processor 206 and memory 208. Processor 206 may be a general purpose or specific purpose processor, an application specific integrated circuit (ASIC), one or more field programmable gate arrays (FPGAs), a group of processing components, or other suitable processing components. Processor 506 may be configured to execute computer code or instructions stored in memory 508 or received from other computer readable media (e.g., CDROM, network storage, a remote server, etc.).

Memory 208 may include one or more devices (e.g., memory units, memory devices, storage devices, etc.) for storing data and/or computer code for completing and/or facilitating the various processes described in the present disclosure. Memory 208 may include random access memory (RAM), read-only memory (ROM), hard drive storage, temporary storage, non-volatile memory, flash memory, optical memory, or any other suitable memory for storing software objects and/or computer instructions. Memory 208 may include database components, object code components, script components, or any other type of information structure for supporting the various activities and information structures described in the present disclosure. Memory 508 may be communicably connected to processor 206 via processing circuit 204 and may include computer code for executing (e.g., by processor 206) one or more processes described herein.

Still referring to FIG. 13, controller 200 is shown to receive input from an imaging device 102. The imaging device acquires all of the imaging data and records it, along with all of the meta-data which describes it. The imaging device will then serialize the data into a stream which can be read by controller 200. The data stream may accommodate any binary data stream type such as the file system, a RDBM or direct TCP/IP communications. For use of the data stream, controller 200 is shown to include a spectral unmixer 210. The spectral unmixer 210 may receive image data from an imaging device 102 on which it performs spectral unmixing to unmix an image presenting various wavelengths into individual, discrete channels for each band of wavelengths. For example, the image data may be "unmixed" into separate channels for each of the various fluorophores used to identify cells or proteins of interest in the tissue sample. The fluorophore, by way of example only, may be one or more of the group consisting of DAPI, Cy® 2, Cy® 3, Cy® 3,5, Cy® 5, FITC, TRITC, Alexa Fluor® 488, Alexa Fluor® 555, Alexa Fluor® 594, and Texas Red. In one example, one of the channels may include image data that falls within a predetermined band surrounding a wavelength of 461 nm (the maximum emission wavelength for DAPI), to identify nuclei in the image. Other channels may include image data for different wavelengths to identify different portions of the tissue sample using different fluorophores.

Controller 200 is also shown to include various maskers, such as cell masker 212, subset area masker 216, and biomarker masker 222. These, or other maskers that may be included in the controller 200 in other embodiments, are used to receive an unmixed signal from the spectral unmixer 210 and create a mask for the particular cell or area of interest, dependent on the fluorophore used to identify certain features of interest in the tissue sample. To create a mask, the maskers (such as cell masker 212, subset area masker 216, and biomarker masker 222) receive image data related to an intensity of each pixel in the field of view. Pixel intensity is directly proportional to the amount of fluorescence emitted by the sample, which in turn, is directly proportional to the amount of protein biomarker in the sample (when using a fluorophore to identify a particular biomarker). An absolute threshold may be set based on the values which exist in the image pixels. All the pixels which are greater than or equal to the threshold value will be mapped to 1.0, or "on", and all other pixels will be mapped to 0.0, or "off." In this way, a binary mask is created to identify the cell or tissue portion of interest in the field of view. In other embodiments, a mask is created using a lower bound wherein all pixels with an intensity at or above a lower bound are accepted and used as the pixel value for the mask. If the intensity is below the lower bound, the pixel value is set to 0.0, or "off".

Figure 14:
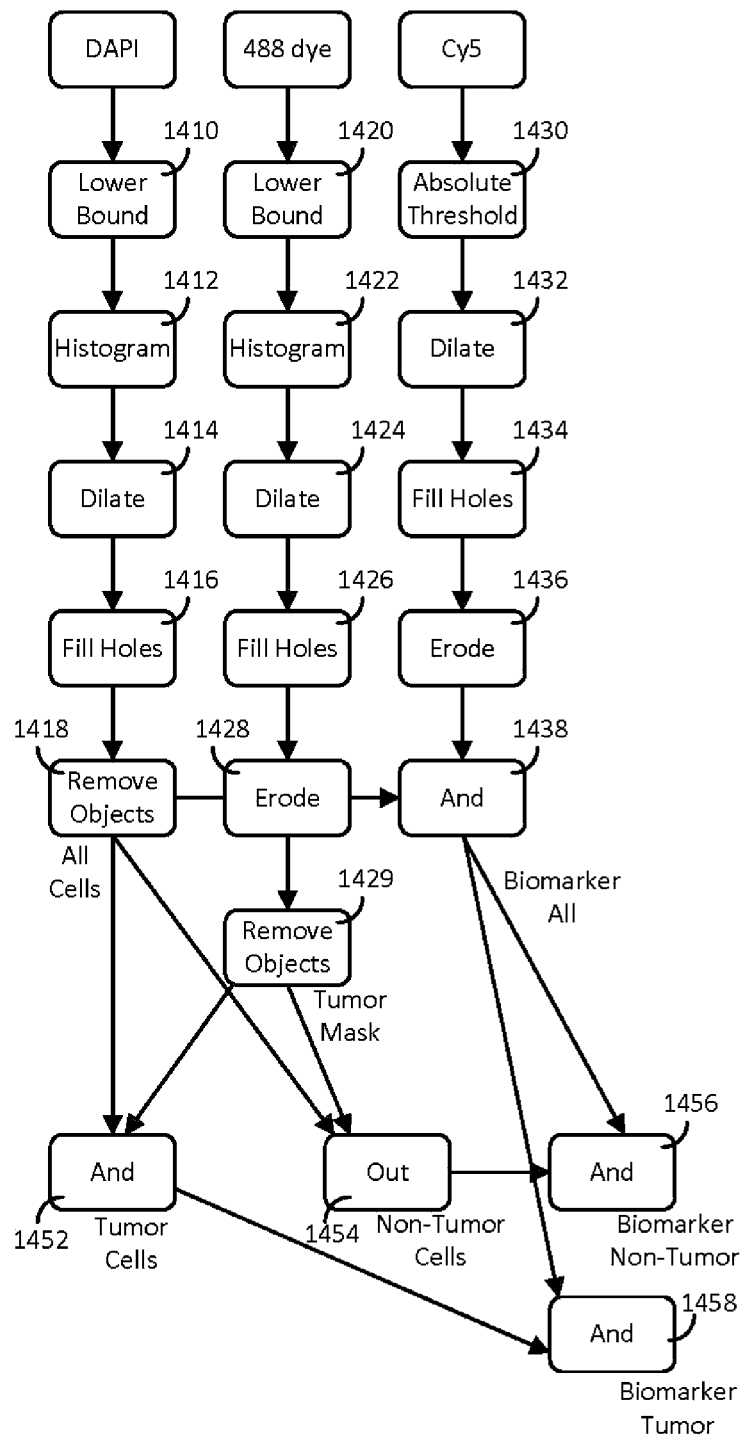
FIG. 14 is a flow diagram of the image processing steps used to derive a value of biomarker positivity, according to an exemplary embodiment.

In the example flow diagram for masking shown in FIG. 14, it is shown that the DAPI and 488 dye channels (or other fluorophore for identifying nuclei and tumor areas, respectively) use the lower bound protocol (steps 1410, 1412, 1420, 1422), while the Cy5 channel (or other fluorophore for identifying a biomarker of interest) uses a threshold value protocol (step 1430), for providing the mask output. In association with the lower bound protocol, there is also a histogram step to determine the lower bound. In particular, histogram threshold (step 1412, 1422) produces a threshold of an input image but uses a sliding scale to determine the point at which the thresholding occurs. The inputs are the current image and a user defined threshold percentage. The latter is used to determine at what percent of the total intensity the threshold level should be set. Firstly, the intensity of every pixel is summed into a total intensity. The threshold percentage is multiplied by this total intensity to obtain a cut-off sum. Finally, all pixels are grouped by intensity (in a histogram) and their intensities summed from lowest to highest (bin by bin) until the cut-off sum is achieved. The last highest pixel intensity visited in the process is the threshold for the current image. All pixels with intensities greater than that value have their intensities set to maximum while all others are set to the minimum.

The steps identified as steps 1414, 1416, 1424, 1426, 1428, 1432, 1434, 1436 in FIG. 14 represent intermediary steps that occur in the initial maskers, such as cell masker 212 (steps 1414, 1416), subset area masker 216 (steps 1424, 1426, 1428), and biomarker masker 222(steps 1432, 1434, 1436). These steps are defined as follows:

Dilate increases the area of brightest regions in an image. Two inputs are need for dilate. The first is the implicit current image and the second is the number of iterations to dilate. It is assumed that only binary images are used for the first input. The procedure will operate on continuous images, but the output will not be a valid dilate. The dilate process begins by first finding the maximum pixel intensity in the image. Subsequently, each pixel in the image is examined once. If the pixel under investigation has intensity equal to the maximum intensity, that pixel will be drawn in the output image as a circle with iterations radius and centered on the original pixel. All pixels in that circle will have intensity equal to the maximum intensity. All other pixels are copied into the output image without modification.

The fill holes procedure will fill "empty" regions of an image with pixels at maximum intensity. These empty regions are those that have a minimum intensity and whose pixel area (size) is that specified by the user. The current image and size are the two inputs required. Like dilate this procedure should only be applied to binary images.

Erode processes images in the same fashion as dilate. All functionality is the same as dilate except that the first step determines the minimum intensity in the image, only pixels matching that lowest intensity are altered, and the circles used to bloom the found minimum intensity pixels are filled with the lowest intensity value. Like dilate this procedure should only be applied to binary images.

Remove Objects. Two inputs are expected: the current image and object size. Remove objects is the opposite of the fill holes procedure. Any regions containing only pixels with maximum intensity filling an area less than the input object size will be set to minimum intensity and thusly "removed." This procedure should only be applied to binary images; application to continuous images may produce unexpected results.

The output at steps 1418, 1429, and 1438 are the resultant cell mask, subset mask (or, in this particular example, tumor area mask), and biomarker cell mask, respectively. FIG. 14 further depicts the combinations of these resultant masks to obtain the relevant area information for the PBP score. These combinations are described below with reference to the combination maskers of the controller 200, depicted in FIG. 13.

Controller 200 is shown to include combination maskers, such as subset cell masker 218, non-subset cell masker 220, and combination masker 230. In some embodiments, the subset cells identified by masker 218 and the non-subset cells identified by masker 220 are tumor cells and non-tumor cells, respectively. Subset cell masker performs an And operation, as shown at step 1452 in FIG. 14, to combine the output of the cell masker 212 (representative of all cells in the image) with the output of the subset area masker 216. Accordingly, subset cell masker generates a mask of all subset cells in the image. This same combination, using an Out operation performed by non-subset cell masker 220 as shown at step 1454 in FIG. 14, generates a mask of all non-subset cells in the sample image.

Combination masker 230 is configured to combine two input masks. As depicted in FIG. 14, combination masker 230 combines the biomarker mask with one of the subset cell mask (from subset cell masker 218) or non-subset cell mask (from non-subset cell masker 220), or both biomarker mask+subset mask and biomarker mask+non-subset mask. The dotted lines represent that either one or both of the cell masks may be combined with the biomarker mask at combination masker 230. The result of the combination masker 230 is a mask representative of all subset cells that are positive for the biomarker and/or all non-subset cells that are positive for the biomarker. The combination masker 230 may combine the masks in an alternate manner such that the result of the combination masker 230 is a mask representative of subset cells that are not positive for the biomarker (biomarker negative). If the cells of interest are not specifically related to the subset, for example tumor or non-tumor, but rather, all cells, then the biomarker positive mask is not combined with any additional mask and passes through the combination masker 230 without modification.

To calculate the % biomarker positivity score (PBP), the area of the selected subset cell (e.g., all, tumor, or non-tumor) biomarker positive mask or biomarker negative mask (in which case the score represents biomarker negativity) is determined in pixels at the area evaluator 232. The total area of all the selected cells (positive and negative for the biomarker), is determined in pixels at the area evaluator 232. The dotted lines terminating at area evaluator 232 indicate that the total area inputs may be one or more of the all cell mask, the subset cell mask, and the non-subset cell mask, to be calculated separately. A percent biomarker positivity score is determined at the positivity calculator 236. In one embodiment, the BPB score is calculated by dividing the area of the selected cell biomarker positive mask from area evaluator 232 by the area of the all selected cell mask from area evaluator 232, and multiplying 100. In one embodiment, the equation executed by the interaction calculator 236 is:

$$BPB = \frac{A_P}{A_A} \times 100$$

wherein $A_P$ is a biomarker positive area for the selected type of subset cell (e.g., all, tumor, or non-tumor) and $A_A$ is the total area of all cells of the selected cell type (all, tumor, non-tumor) Similarly, AN could replace $A_P$ in the above equation, wherein $A_N$ is a biomarker negative area for the selected type of cell (e.g., all, tumor, or non-tumor), to determine a score representative of percent biomarker negativity for the type of subset cell.

The And procedure is modeled after a binary AND operation, but differs in significant ways. And accepts the current image and a user selected resultant. The output is an image created by performing a multiplication of the normalized intensities of matching pixels from the two input images. In some cases, image intensity data is already normalized. Therefore, the And procedure is simply a pixelwise multiplication of the two images. The two inputs required for Out are the current image and a user selected resultant. Out removes the second image form the first according to the formula $A*(1-B/B_{max})$ where A is the current image, B the user selected image to remove, and $B_{max}$ is the maximum intensity of B. Note that the division of B by $B_{max}$ normalizes B.

EXAMPLES

Example 1. Sample Preparation, Imaging, and Analysis of Imaging for Melanoma Tissue Samples from Human Patients Sample Preparation.

Figure 1:
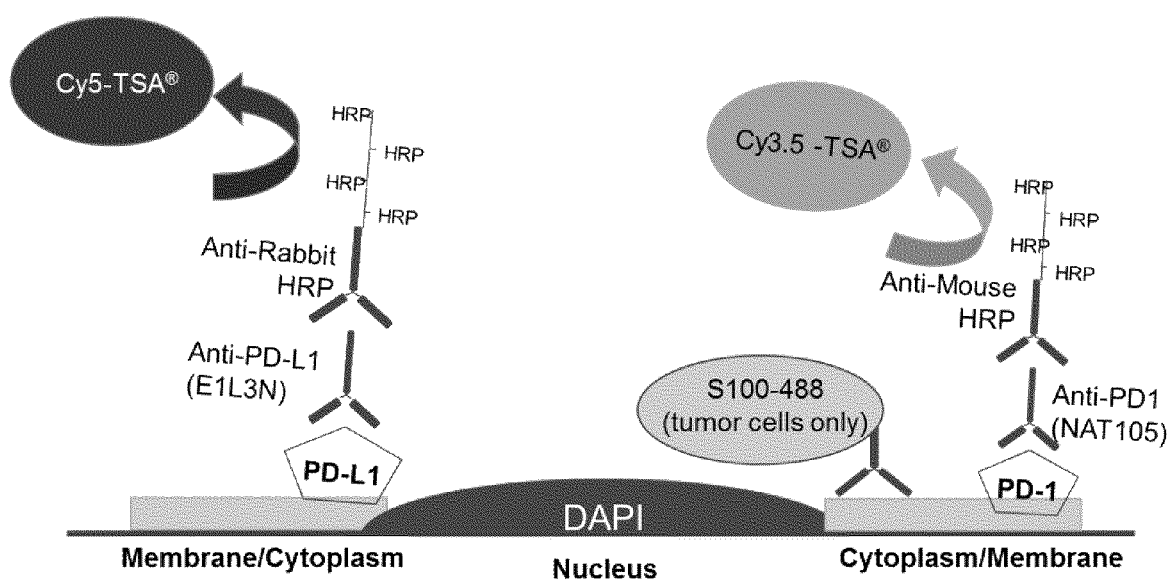
FIG. 1 shows a non-limiting example of an overview of antibodies and detection reagents used in the preparation of tissue samples for imaging and analysis.

Formalin fixed paraffin embedded (FFPE) tissue samples were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining. Next, the slides were stained with a mouse anti-PD1 primary antibody. Slides were then washed before incubation with an anti-mouse HRP secondary antibody. Slides were washed and then PD-1 staining was detected using TSA+Cy® 3.5 (Perkin Elmer). Any residual HRP was then quenched using two washes of fresh 100 mM benzhydrazide with 50 mM hydrogen peroxide. The slides were again washed before staining with a rabbit anti-PD-L1 primary antibody. Slides were washed and then incubated with a cocktail of anti-rabbit HRP secondary antibody plus mouse anti-S100 directly labeled with 488 dye and 4',6-diamidino-2-phenylindole (DAPI). Slides were washed and then PD-L1 staining was detected using TSA-Cy® 5 (Perkin Elmer). Slides were washed a final time before they were cover-slipped with mounting media and allowed to dry overnight at room temperature. A schematic overview of the antibodies and detection reagents is shown in FIG. 1.

Sample Imaging and Analysis.

Fluorescence images were then acquired using the Vectra 2 Intelligent Slide Analysis System using the Vectra software version 2.0.8 (Perkin Elmer). First, monochrome imaging of the slide at 4× magnification using DAPI was conducted. An automated algorithm (developed using inForm) was used to identify areas of the slide containing tissue.

The areas of the slide identified as containing tissue were imaged at 4× magnification for channels associated with DAPI (blue), FITC (green), and Cy® 5 (red) to create RGB images. These 4× magnification images were processed using an automated enrichment algorithm (developed using inForm) in field of view selector 104 to identify and rank possible 20× magnification fields of view according to the highest Cy® 5 expression.

The top 40 fields of view were imaged at 20× magnification across DAPI, FITC, Texas Red, and Cy® 5 wavelengths. Raw images were reviewed for acceptability, and images that were out of focus, lacked any tumor cells, were highly necrotic, or contained high levels of fluorescence signal not associated with expected antibody localization (i.e., background staining) were rejected prior to analysis. Accepted images were processed using AQUAduct (Perkin Elmer), wherein each fluorophore was spectrally unmixed by spectral unmixer 210 into individual channels and saved as a separate file.

The processed files were further analyzed using AQUAnalysis™ or through a fully automated process using AQUAserve™. Details were as follows.

Figure 2A:
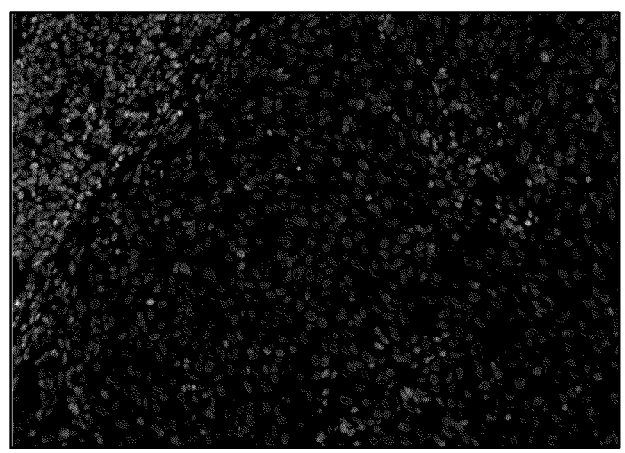
FIG. 2a shows a non-limiting example of all nuclei detected with DAPI within an image.
Figure 2B:
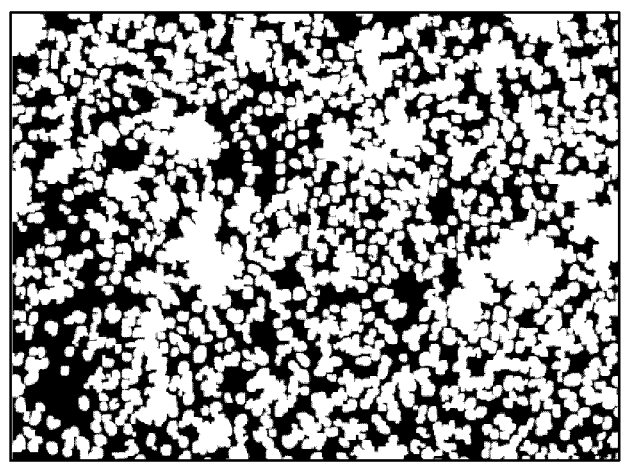

Each DAPI image was processed by cell masker 212 to identify all cell nuclei within that image (FIG. 2a), and then dilated by 3 pixels to represent the approximate size of an entire cell. This resulting mask represented all cells within that image (FIG. 2b).

Figure 3A:
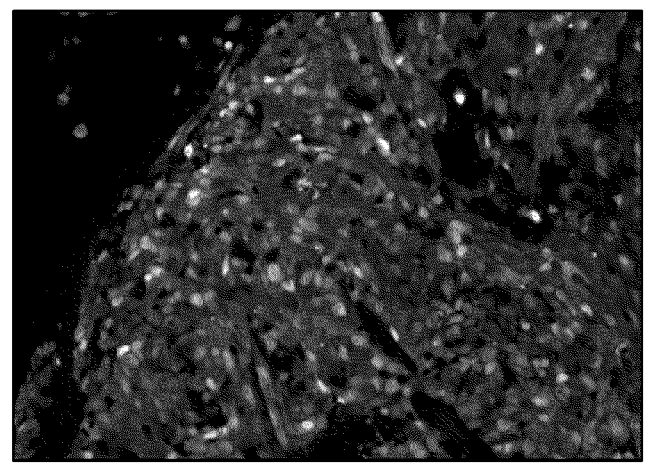
FIG. 3a shows a non-limiting example of an image of S100 detected with 488 dye.
Figure 3B:
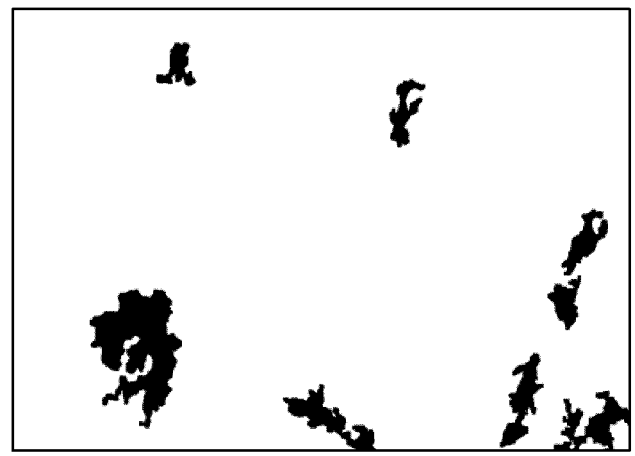
Figure 3C:
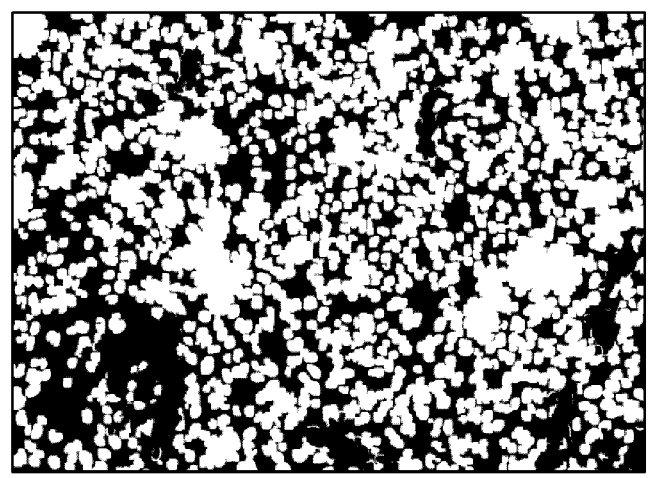

S100 (tumor cell marker for melanoma) detected with 488 dye (FIG. 3a) was processed by tumor masker 216 to create a binary mask of all tumor area within that image (FIG. 3b). Overlap between this mask and the mask of all cells created a new mask for tumor cells (FIG. 3c).

Similarly, absence of the tumor cell marker in combination with the mask of all nuclei created a new mask for all non-tumor cells (FIG. 3d), performed by non-tumor cell masker 220.

Figure 4A:
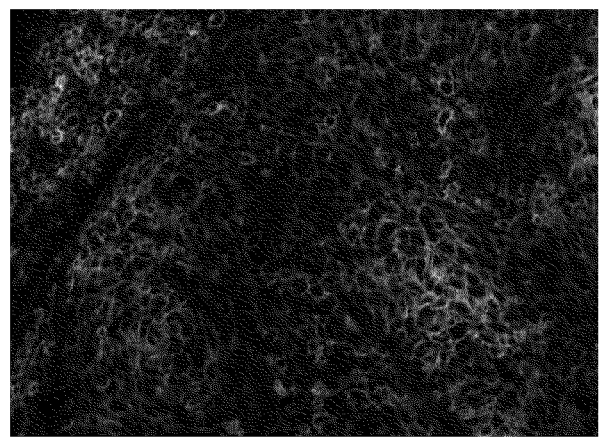
FIG. 4a shows a non-limiting example of an image of PD-L1 detected with Cy® 5.
Figure 4B:
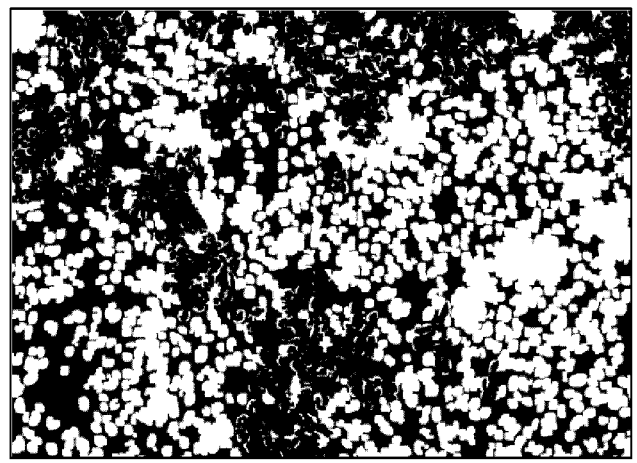
Figure 4C:
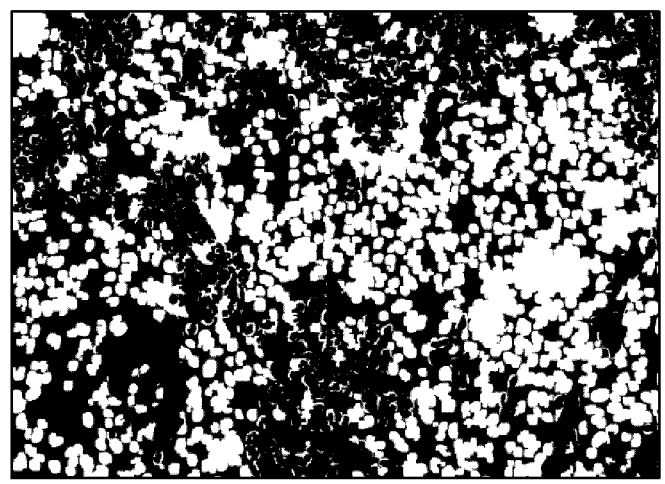
Figure 4D:

Each Cy® 5 image (FIG. 4a) was processed by biomarker masker 222 to create a binary mask of all cells that are PD-L1-positive (FIG. 4b). Overlap between the mask of all tumor cells and the mask of all PD-L1-positive cells, using combination masker 230, created a new mask of all PD-L1-positive tumor cells (FIG. 4c). Similarly, overlap between the mask of all non-tumor cells and the mask of all PD-L1-positive cells, using combination masker 230, created a new mask of all PD-L1-positive non-tumor cells (FIG. 4d).

Figure 5A:
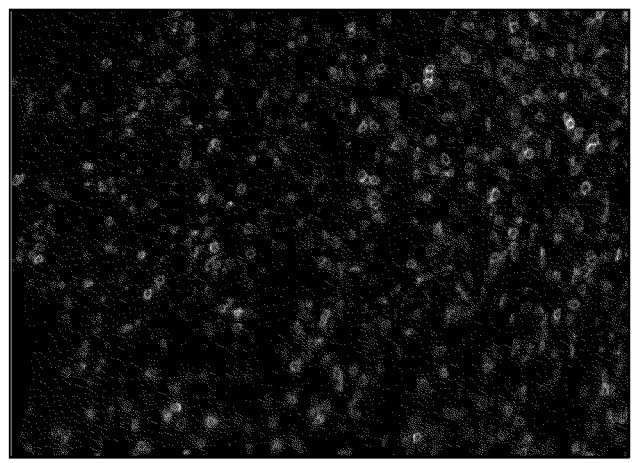
FIG. 5a shows a non-limiting example of an image of PD-1 detected with Cy® 3.5.
Figure 5B:
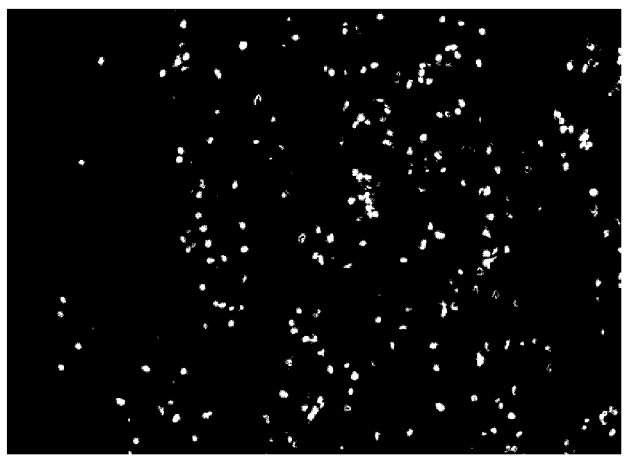

Each Cy® 3.5 image (FIG. 5a) was overlapped with the mask of all non-tumor cells to create a binary mask of all cells that are PD-1-positive (FIG. 5b).

Figure 6A:
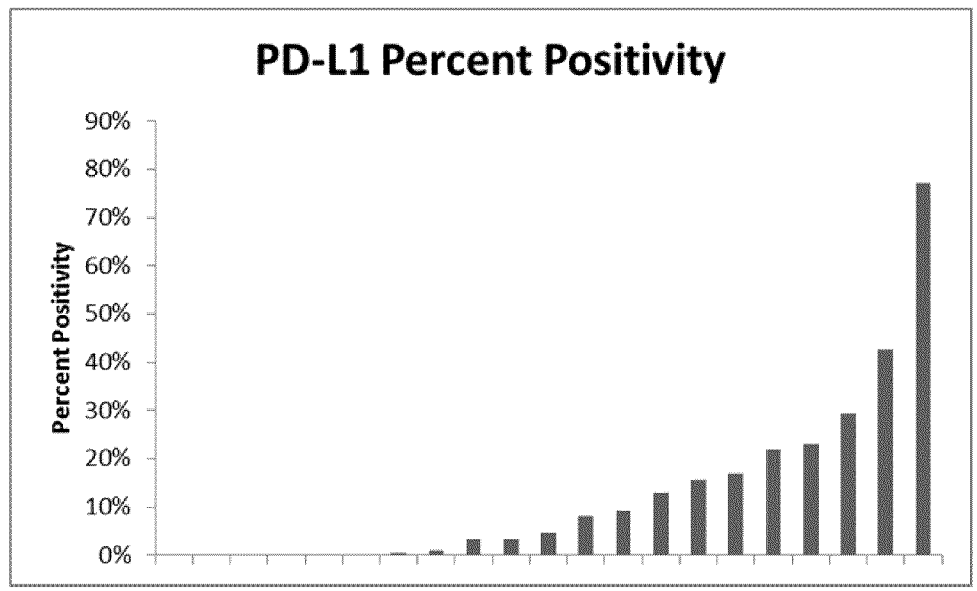
FIG. 6a shows a non-limiting example of values of % biomarker positivity (PBP) for all cells expressing PD-L1 in tissue samples from 21 melanoma patients, sorted by increasing PD-L1 expression.

The % biomarker positivity (PBP) for all tumor cells expressing PD-L1 was derived, using positivity calculator 236, by dividing the total area, measured in pixels and determined by area evaluator 232, of the mask of all PD-L1-positive tumor cells (FIG. 4c) with the total area, measured in pixels and determined by area evaluator 232, of the mask of all tumor cells (FIG. 3c). Representative values of PBP for all cells expressing PD-L1 are shown in FIG. 6a (data sorted according to increasing expression).

Figure 3D:
Figure 6B:
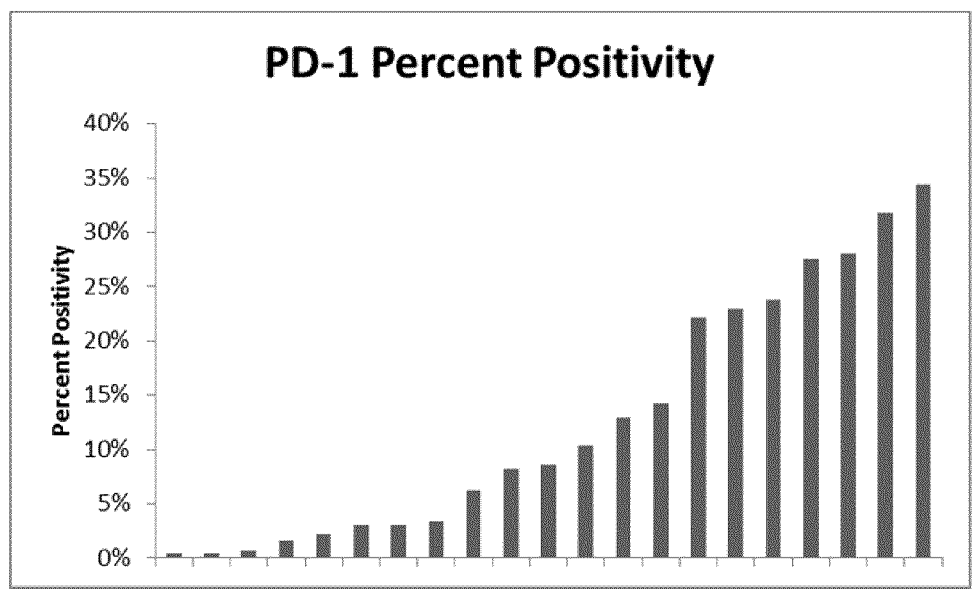
FIG. 6b shows a non-limiting example of values of PBP for all non-tumor cells expressing PD-1 in tissue samples from the same 21 melanoma patients, sorted by increasing PD-1 expression.

The PBP for all non-tumor cells expressing PD-1 was derived by dividing the total area, measured in pixels, of the mask of all PD-1-positive non-tumor cells (FIG. 5b) with the total area, measured in pixels, of the mask of all non-tumor cells (FIG. 3d). Representative values of PBP for all non-tumor cells expressing PD-1 are shown in FIG. 6b (data sorted according to increasing expression).

Figure 7:
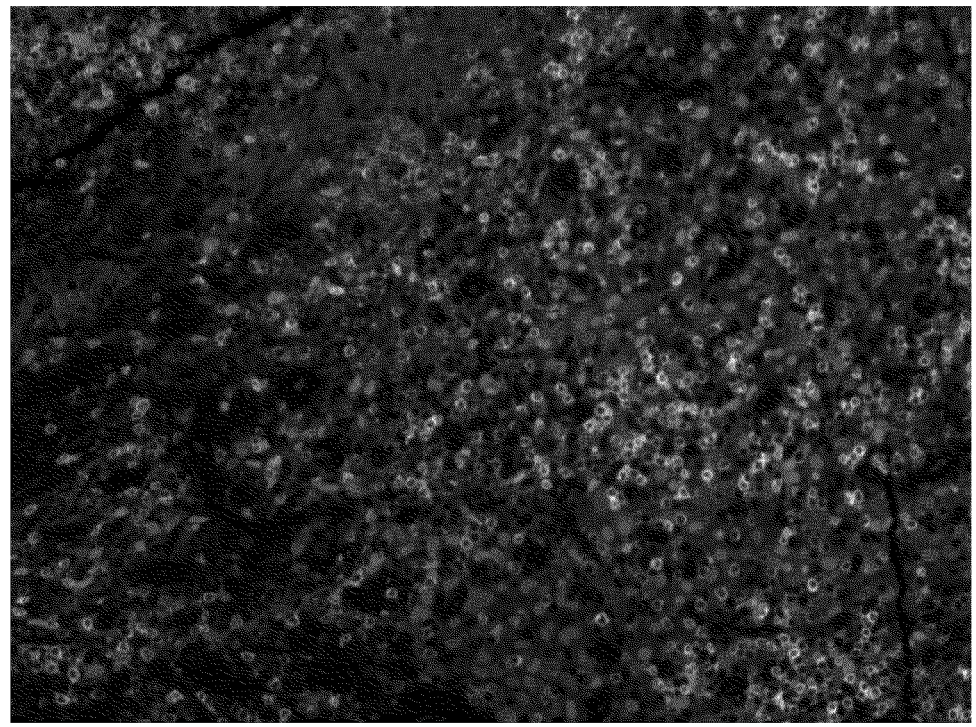
FIG. 7 shows a non-limiting example of a mask of fluorescence signals corresponding to PD-L1-positive cells (red), PD-1-positive cells (yellow), all tumor cells (green), and all cells (blue) for a positive responder to immunotherapy.
Figure 8:
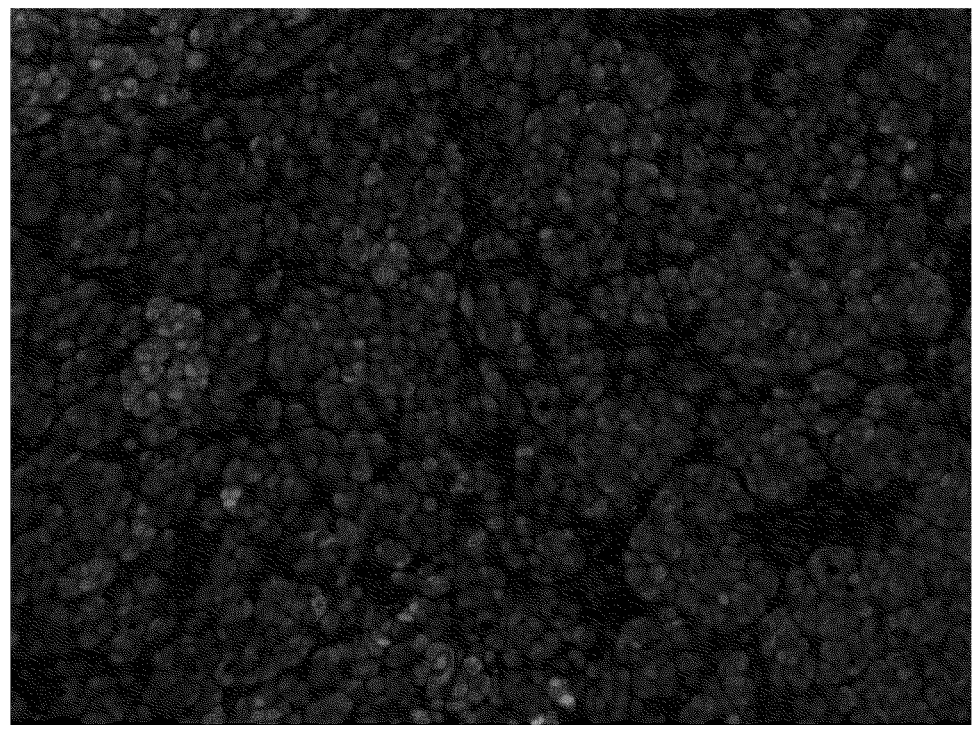
FIG. 8 shows a non-limiting example of a mask of fluorescence signals corresponding to PD-L1-positive cells (red), PD-1-positive cells (yellow), all tumor cells (green), and all cells (blue) for a negative responder to immunotherapy.

FIGS. 7 and 8 show representative examples of overlaid masks indicating PD-L1-positive cells (red), PD-L-positive cells (yellow), tumor cells (S100, green), and all cells (DAPI, blue). For a positive responder to immunotherapy, the mask in FIG. 7 readily indicates the presence of PD-L1-positive cells (red), PD-1-positive cells (yellow), and all tumor cells (green). In contrast, for a negative responder to immunotherapy, the mask in FIG. 8 indicates the presence of tumor cells (S100, green) and all cells (DAPI, blue), but shows little to no PD-L1-positive cells (red) or PD-1-positive cells (yellow).

Figure 9:
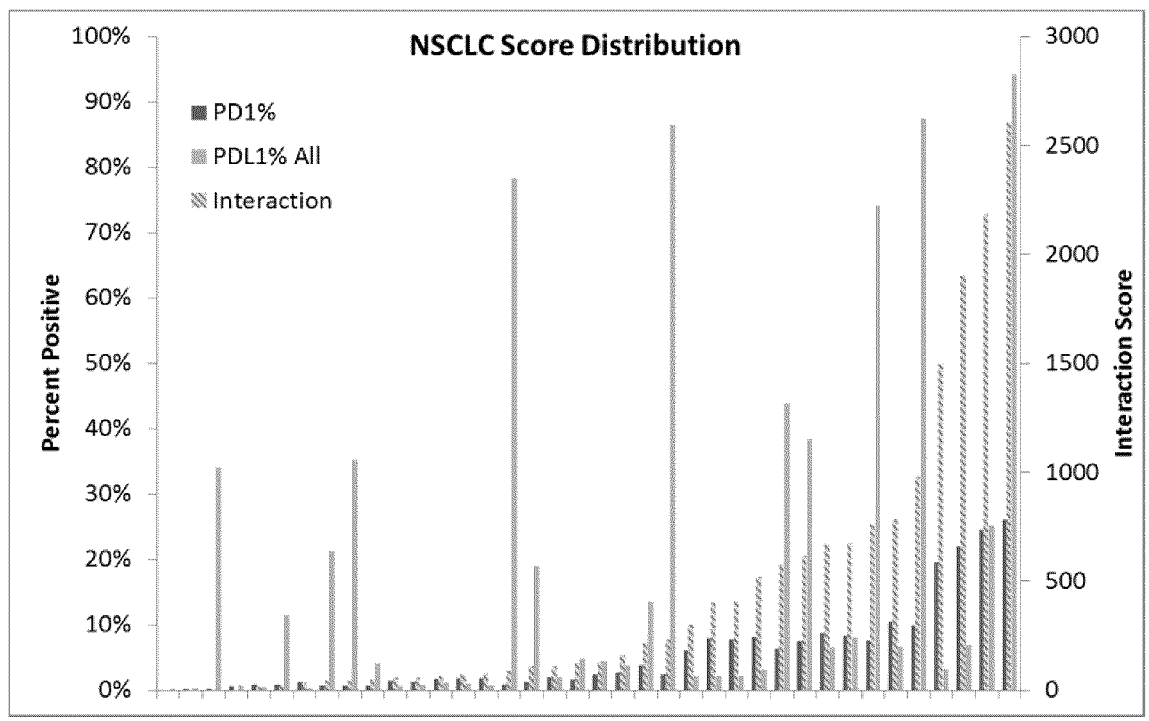
FIG. 9 shows values of % biomarker positivity (PBP) for PD-L1 and PD-1 from 38 non-small cell lung cancer patients.

Example 2 Sample Preparation, Imaging, and Analysis of Imaging for Non-Small Cell Lung Carcinoma (NSCLC) Tissue Samples from Human Patients Analogous procedures as Example 1 were performed, substituting the mouse anti-S100 directly labeled with 488 dye with a mouse anti-pan cytokeratin directly labeled with 488 dye for epithelial tumor samples. PBP values for PD-1 and PD-L1 are shown in FIG. 9. A subset of these patients exhibited high levels of receptor-ligand interaction reminiscent of immune suppression.

Example 3. Comparison of Analysis Techniques

Figure 10:
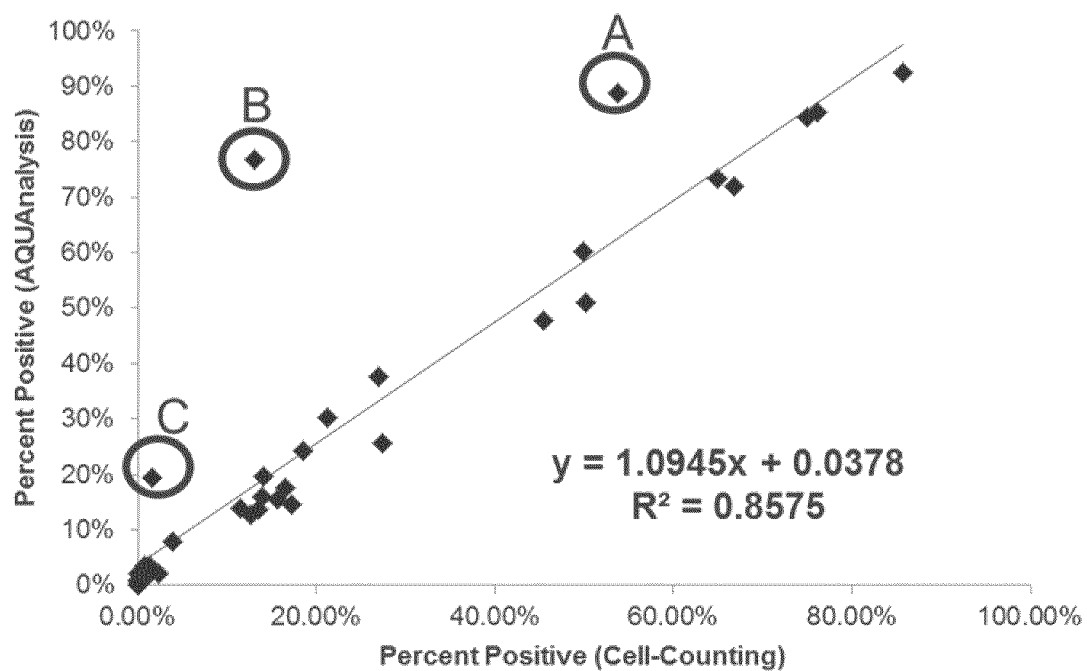
FIG. 10 shows a comparison of % PD-L1 positivity as ascertained by an automated cell counting method versus a method described herein.

To generate control specimens, lymphoma cell lines with previously established expression of PD-L1 (Karpas 299) or lack of expression (Ramos RA#1) were cultured according to manufacturer's instructions. The cells were then counted and the two cell lines were mixed at varying percentages to generate a series of FFPE cell line pellet block ranging in PD-L1 expression from 0-100%. Cores (600 μm) from these cell line mixtures as well as from normal tonsil tissue resections were then used to create a tissue microarray (TMA). A section of this TMA was then stained, imaged and each core was then scored for % PD-L1 positivity using AQUAnalysis™ (all steps as described in Example 1) and the results are shown on the Y-axis of FIG. 10, where each point represents a single core (single field of view).

Alternatively, the same images were quantified for % PD-L1 expression using a cell counting based software for comparison as follows. DAPI was used to first identify each cell nuclei and a morphological cytoplasm was then created surrounding the identified cell nuclei. An intensity threshold was established to identify cells with PD-L1 expression in the cytoplasm of the cells. The total number of cells identified above this threshold was then divided by the total number of cells in the image to determine the % PD-L1 positive cells in each core and the results are shown on the X-axis of FIG. 10. Overall, there was a high level of concordance between the two methods of cell counting (R2=0.86, slope 1.1); however, there were three noticeable outliers labeled as A, B, C in FIG. 10 where the % PD-L1 positivity determined by AQUA® scoring was significantly higher than that of the cell counting method. Points A and B were cell line cores where 100% of the cells were Karpas299 and thus values determined by AQUA® scoring were much closer to expected and the cell counting method failed to identify the cytoplasm of the cells as PD-L1 positive. Similarly, in point C, the cell mixture included a theoretical 40% of Karpas299 cells where the value determined by AQUA® scoring was again much closer to expected over the cell counting method. These results demonstrated the superiority of methods disclosed herein over the cell counting based software.

Example 4. Sample Preparation, Imaging, and Analysis of Imaging for Tissue Samples with Cells Expressing PD-L1 and Cells Expressing CD80

Analogous procedures as Example 1 are performed, substituting the staining and analysis of PD-1 with the staining and analysis of CD80.

Example 5. Sample Preparation, Imaging, and Analysis of Imaging for Tissue Samples with Cells Expressing CTLA-4 and Cells Expressing C80

Sample Preparation

Formalin fixed paraffin embedded (FFPE) tissue samples were dewaxed, rehydrated and antigen retrieval was performed with elevated temperature conditions. Staining was then performed where the following steps were carried out. First, tissues were subjected to CTLA-4 expression detection using 20 pairs of hybridization probes spanning approximately 1 kb of the CTLA-4 mRNA using RNAScope® (Advanced Cell Diagnostics). In situ hybridization was visualized with TSA-Cy® 3. The slides were washed and any residual HRP was then quenched using two washes of fresh 100 mM benzhydrazide with 50 mM hydrogen peroxide. The slides were again washed before staining with a mouse anti-CD80 primary antibody. Slides were washed and then incubated with an anti-mouse HRP secondary antibody. Slides were washed and then CD80 staining was detected using TSA-Cy® 5 (Perkin Elmer). Any residual HRP was then quenched using two washes of fresh 100 mM benzhydrazide with 50 mM hydrogen peroxide. The slides were again washed before staining with a rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected using TSA-AlexaFluor488® (Life Technologies). Slides were washed a final time before they were cover-slipped with mounting media and allowed to dry overnight at room temperature.

Figure 31A:
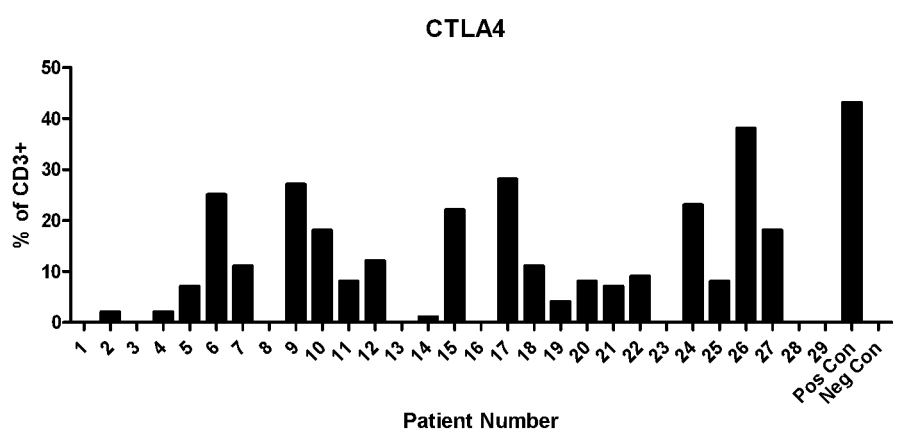
FIG. 31a shows a non-limiting example of quantitative assessment of CTLA-4 in T cells on melanoma tissues.
Figure 31B:
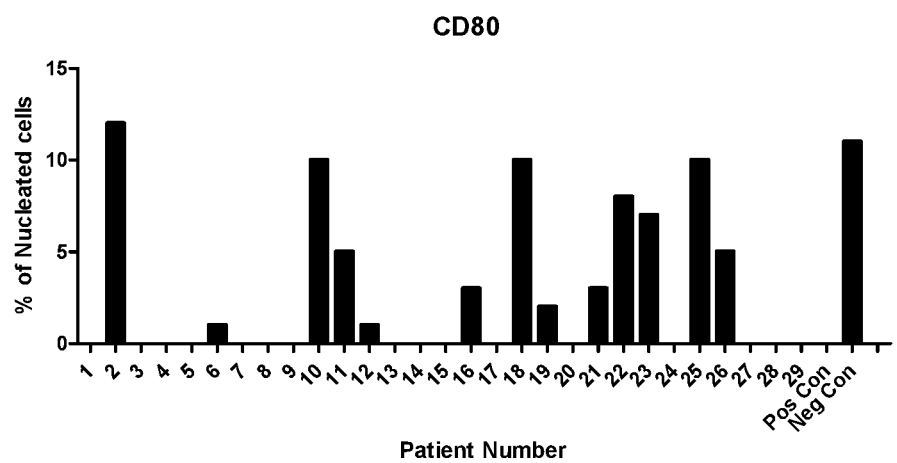
FIG. 31b shows a non-limiting example of quantitative assessment of CD80 on melanoma tissues.

Analogous imaging and analysis procedures as Example 1 were performed, imaging across DAPI, FITC, Cy® 3, and Cy® 5 wavelengths. Expression of CTLA-4 and CD80 was used to develop an enrichment algorithm for acquiring 20× images. Analysis was performed to survey the prevalence of CTLA-4 in CD3 positive T cells and CD80 expression in tumor samples taken from patients with metastatic melanoma. Results are shown in FIGS. 31*a* and 31*b*.

Example 6. Sample Preparation, Imaging, and Analysis of Imaging for Tissue Samples with Cells Expressing PD-L2 and Cells Expressing PD-1

Analogous procedures as Example 1 are performed, substituting the staining and analysis of PD-L1 with the staining and analysis of PD-L2.

Example 7. Sample Preparation, Imaging, and Analysis of Imaging for Tissue Samples with Cells Expressing CTLA-4 and Cells Expressing CD86

Analogous procedures as Example 1 are performed, substituting the staining and analysis of PD-L1 and PD-1 with the staining and analysis of CTLA-4 and CD86.

Example 8. Sample Preparation, Imaging, and Analysis of Imaging for Tissue Samples with Cells Expressing LAG-3 and Cells Expressing HLA-DR Analogous procedures as Example 1 are performed, substituting the staining and analysis of PD-L1 and PD-1 with the staining and analysis of LAG-3 and HLA-DR.

Example 9. Sample Preparation, Imaging, and Analysis of Imaging for Tissue Samples with Cells Expressing TIM-3 and Cells Expressing Galectin 9

Analogous procedures as Example 1 are performed, substituting the staining and analysis of PD-L1 and PD-1 with the staining and analysis of TIM-3 and Galectin 9.

Example 10. Sample Preparation, Imaging, and Analysis of Imaging for Tissue Samples with Cells Expressing 41BB and Cells Expressing 4.1BBL Analogous procedures as Example 1 are performed, substituting the staining and analysis of PD-L1 and PD-1 with the staining and analysis of 41BB and 4.1BBL.

Example 11. Sample Preparation, Imaging, and Analysis of Imaging for Tissue Samples with Cells Expressing OX40 and Cells Expressing OX40L Analogous procedures as Example 1 are performed, substituting the staining and analysis of PD-L1 and PD-1 with the staining and analysis of OX40 and OX40L.

Example 12. Sample Preparation, Imaging, and Analysis of Imaging for Tissue Samples with Cells Expressing CD40 and Cells Expressing CD40L Analogous procedures as Example 1 are performed, substituting the staining and analysis of PD-L1 and PD-1 with the staining and analysis of CD40 and CD40L.

Example 13. Sample Preparation, Imaging, and Analysis of Imaging for Tissue Samples with Cells Expressing ICOS and Cells Expressing ICOSL Analogous procedures as Example 1 are performed, substituting the staining and analysis of PD-L1 and PD-1 with the staining and analysis of ICOS and ICOSL.

Example 14. Sample Preparation, Imaging, and Analysis of Imaging for Tissue Samples with Cells Expressing GITR and Cells Expressing GITRL Analogous procedures as Example 1 are performed, substituting the staining and analysis of PD-L1 and PD-1 with the staining and analysis of GITR and GITRL.

Example 15. Sample Preparation, Imaging, and Analysis of Imaging for Tissue Samples with Cells Expressing HLA-DR and Cells Expressing TCR Analogous procedures as Example 1 are performed, substituting the staining and analysis of PD-L1 and PD-1 with the staining and analysis of HLA-DR and TCR.

Example 16. Sample Preparation, Imaging, and Analysis of CD3 and PD-1 on Tissue Samples from Diffuse Large B-Cell Lymphoma (DLBCL) Patients Sample preparation.

Figure 15:
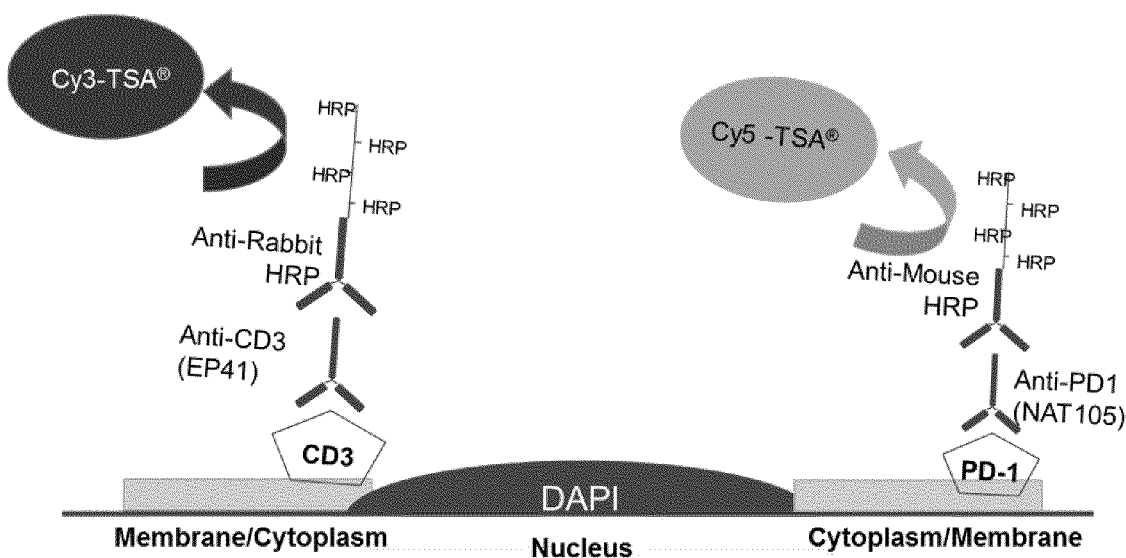
FIG. 15 shows another non-limiting example of an overview of antibodies and detection reagents used in the preparation of tissue samples for imaging and analysis.

Formalin fixed paraffin embedded (FFPE) tissue samples from DLBCL patients (n=43) were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining. Next, the slides were stained with a mouse anti-PD1 primary antibody. Slides were then washed before incubation with an anti-mouse HRP secondary antibody. Slides were washed and then PD-1 staining was detected using TSA+Cy® 3 (Perkin Elmer). Primary and secondary antibody reagents were then removed via microwave. The slides were again washed before staining with a rabbit anti-CD3 primary antibody. Slides were washed and then incubated with a cocktail of anti-rabbit HRP secondary antibody plus 4',6-diamidino-2-phenylindole (DAPI). Slides were washed and then CD3 staining was detected using TSA-Cy® 5 (Perkin Elmer). Slides were washed a final time before they were cover-slipped with mounting media and allowed to dry overnight at room temperature. A schematic overview of the antibodies and detection reagents is shown in FIG. 15.

Sample imaging and analysis. Fluorescence images were then acquired using the Vectra 2 Intelligent Slide Analysis System using the Vectra software version 2.0.8 (Perkin Elmer). First, monochrome imaging of the slide at 4× magnification using DAPI was conducted. An automated algorithm (developed using inForm) was used to identify areas of the slide containing tissue.

The areas of the slide identified as containing tissue were imaged at 4× magnification for channels associated with DAPI (blue), Cy® 3 (green), and Cy® 5 (red) to create RGB images. These 4× magnification images were processed using an automated enrichment algorithm (developed using inForm) in field of view selector 104 to identify and rank possible 20× magnification fields of view according to the highest Cy® 3 expression.

The top 40 fields of view were imaged at 20× magnification across DAPI, Cy® 3, and Cy® 5 wavelengths. Raw images were reviewed for acceptability, and images that were out of focus, lacked any tumor cells, were highly necrotic, or contained high levels of fluorescence signal not associated with expected antibody localization (i.e., background staining) were rejected prior to analysis. Accepted images were processed using AQUAduct (Perkin Elmer), wherein each fluorophore was spectrally unmixed by spectral unmixer 210 into individual channels and saved as a separate file.

The processed files were further analyzed using AQUAnalysis™ or through a fully automated process using AQUAserve™. Details were as follows.

Figure 16A:
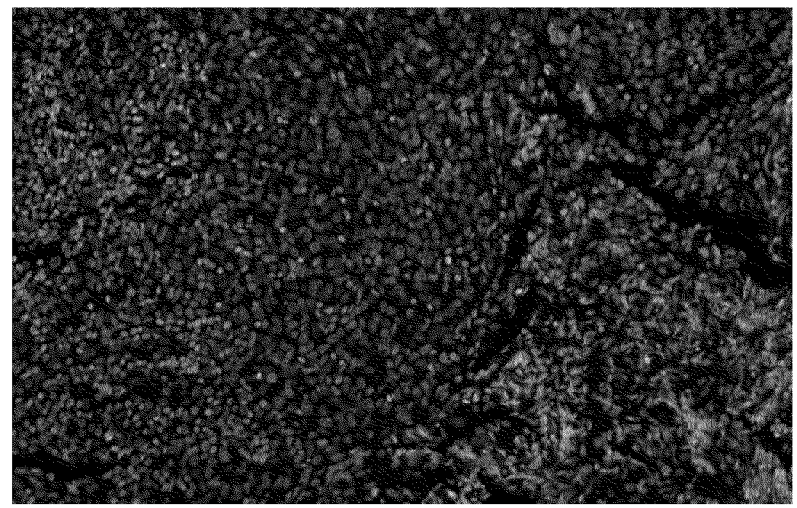
FIG. 16a shows a non-limiting example of a non-limiting example of all nuclei detected with DAPI within an image.
Figure 16B:
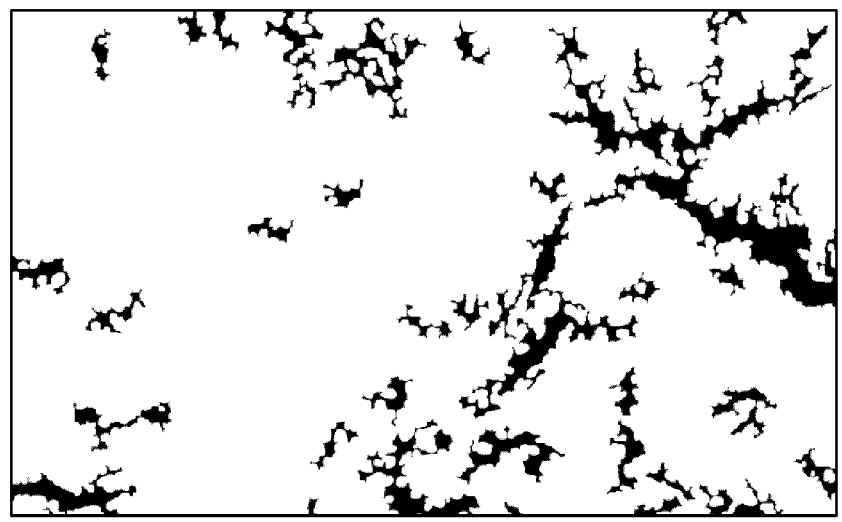

Each DAPI image was processed by cell masker 212 to identify all cell nuclei within that image (FIG. 16a), and then dilated by 2 pixels to represent the approximate size of an entire cell. This resulting mask represented all cells within that image (FIG. 16b).

Figure 17A:
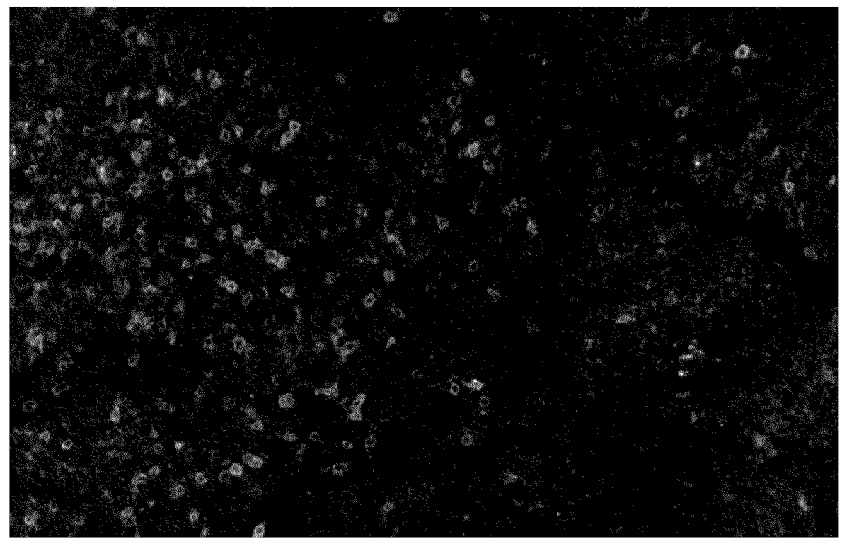
FIG. 17a shows a non-limiting example of an image of PD-1 detected with Cy® 5.
Figure 17B:

Each Cy® 5 image (FIG. 17a) was processed by biomarker masker 222 to create a binary mask of all cells that are PD-1-positive (FIG. 17b).

Figure 18A:
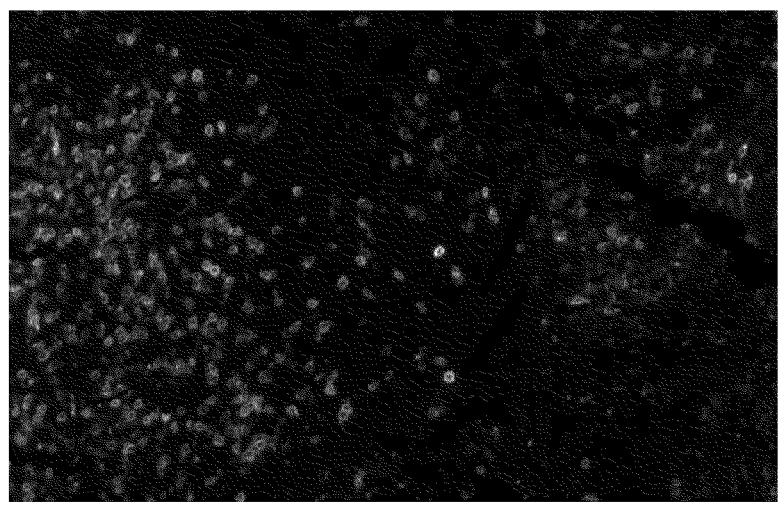
FIG. 18a shows a non-limiting example of an image of CD3 detected with Cy® 3.
Figure 18B:
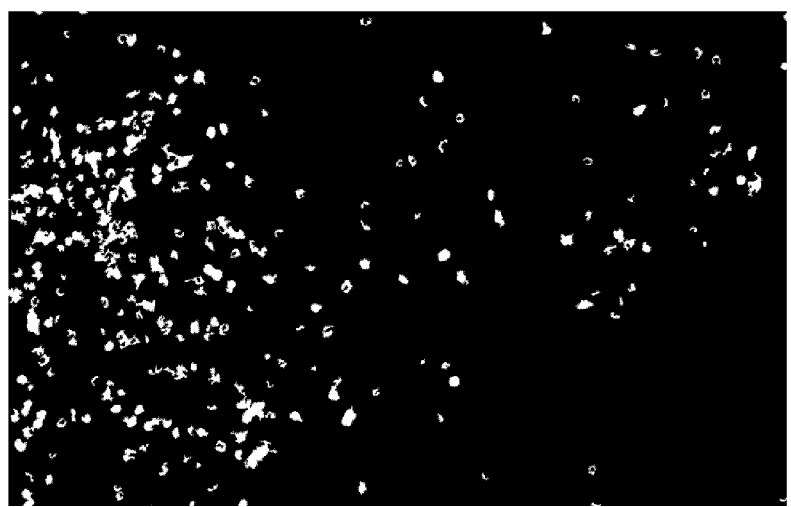

Each Cy® 3 image (FIG. 18a) was processed by biomarker masker 222 to create a binary mask of all cells that are CD3-positive (FIG. 18b).

Figure 19:
FIG. 19 shows a non-limiting example of a binary mask of all cells that are double positive for PD-1 and CD3.

The binary masks for all cells PD-1-positive and CD3-positive were combined to create a binary mask of all cells that are double positive for PD-1 and CD3 (FIG. 19).

Figure 20A:
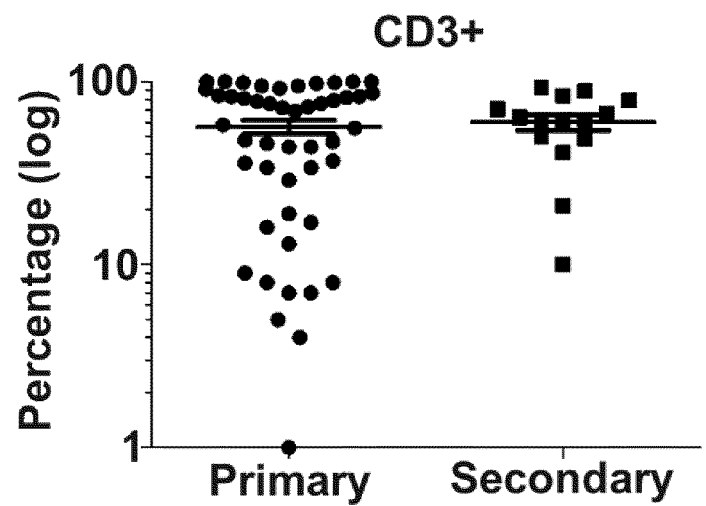
FIG. 20a shows a non-limiting example of quantitative assessment of CD3+ T-cells in tissue samples from DLBCL patients (n=43).
Figure 20B:
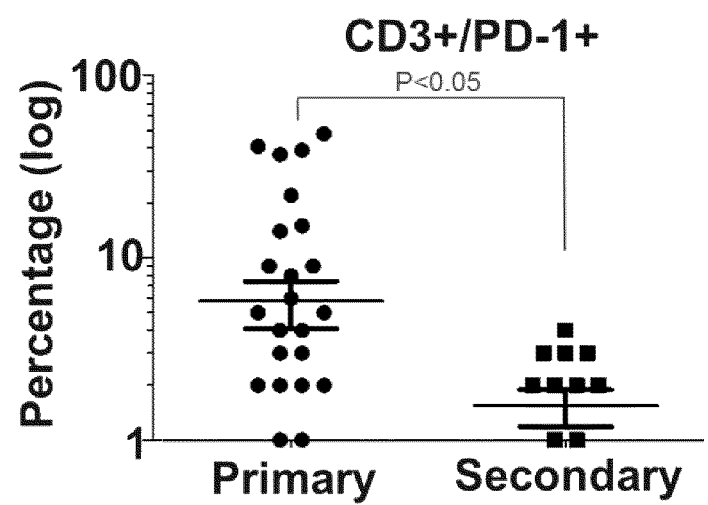
FIG. 20b shows a non-limiting example of quantitative assessment of CD3+/PD1+ T-cells in tissue samples from DLBCL patients (n=43).

The % biomarker positivity (PBP) for all CD3 cells expressing PD-1 was derived, using positivity calculator 236, by dividing the total area, measured in pixels and determined by area evaluator 232, of the mask of all PD-1-positive cells (FIG. 17b) with the total area, measured in pixels and determined by area evaluator 232, of the mask of all CD3-positive cells (FIG. 18b). Differential distribution of exhausted T-cells (CD3+/PD1+) were observed in primary (low levels) versus secondary sites (high levels). Results are shown in FIGS. 20a and 20b.

Example 17. Platform Comparison

The accuracy of analogous procedures as Examples 1 and 16 was confirmed by comparison with flow cytometry. The frequencies of regulatory T-cells (based on FoxP3 and CD25 expression) was ascertained in whole blood stimulated with IL-2, TGF β, and CD28 for 5 days on a CD3-coated plate.

| Platform | FoxP3 | CD25 |
| --- | --- | --- |
| Flow cytometry | 22% | 66% |
| PBP method | 24% | 66% |

Example 18. Assessment of CD25/FoxP3 T-Cells in Multiple Tumor Indications

Figure 21A:
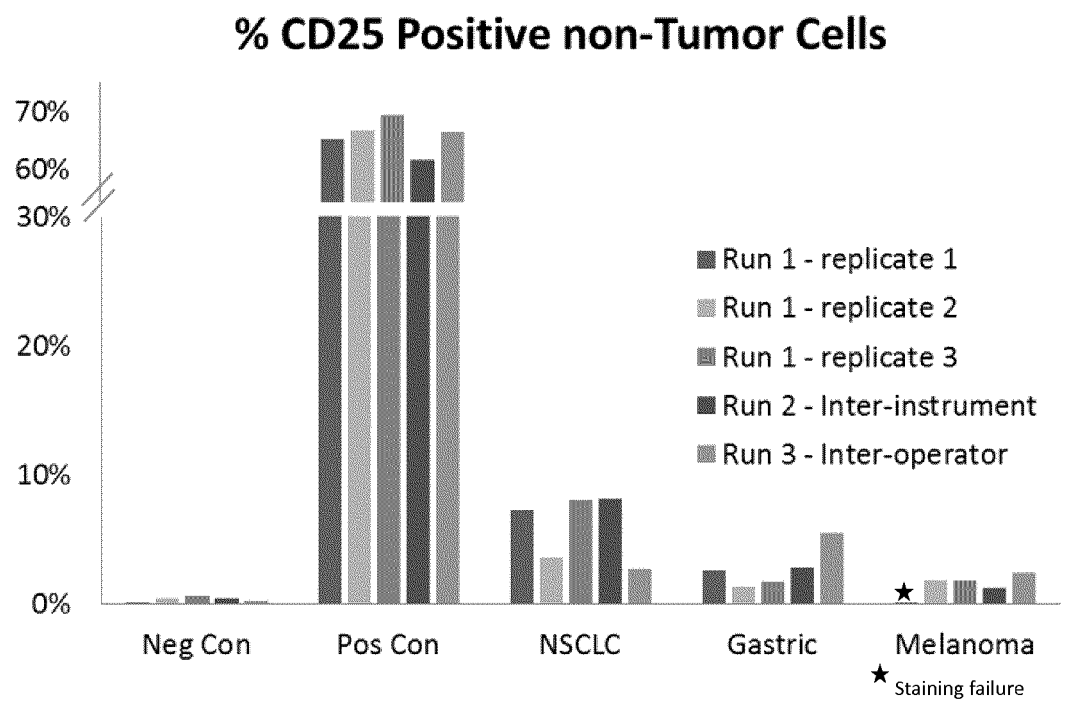
FIG. 21a shows a non-limiting example of quantitative assessment of CD25 on NSCLC, gastric, and melanoma tissues.
Figure 21B:
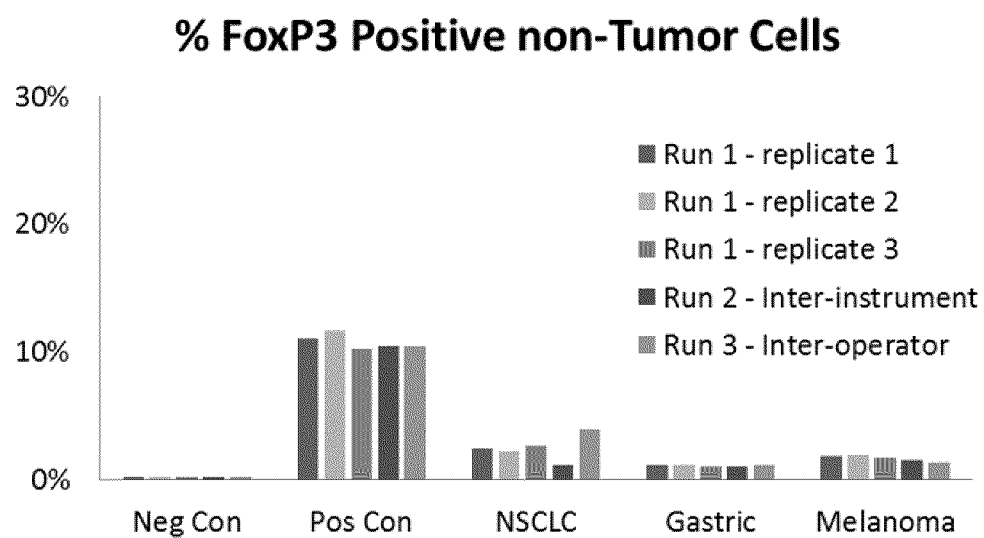
FIG. 21b shows a non-limiting example of quantitative assessment of FoxP3 on NSCLC, gastric, and melanoma tissues.
Figure 22:
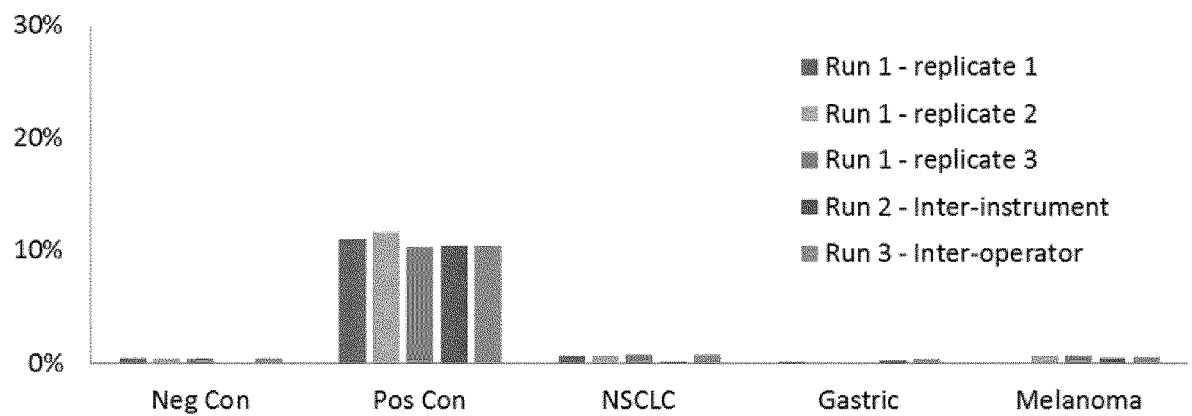
FIG. 22 shows a non-limiting example of quantitative assessment of CD25+/FoxP3+ T-cells in NSCLC, gastric, and melanoma tissues.

Analogous procedures as Example 16 were performed with the additional identification of tumor cells with either anti-S100 or anti-cytokeratin antibodies detected with an AlexaFluor488 secondary antibody and imaged across DAPI, FITC, Cy® 3, and Cy® 5 wavelengths for quantitative assessment of CD25 and FoxP3 on NSCLC, gastric, and melanoma tissues. The tissues were stained with antibodies recognizing CD25 and FoxP3 and their expression in non-tumor areas were calculated as % expression. The prevalence of CD25/FoxP3+ T-cells ranged from 1% to 10% in archival lung, gastric, and melanoma tissue specimens. Results are shown in FIGS. 21 and 22.

Example 19. Assessment of CD4/CD8 T-Cells in Multiple Tumor Indications

Figure 23A:
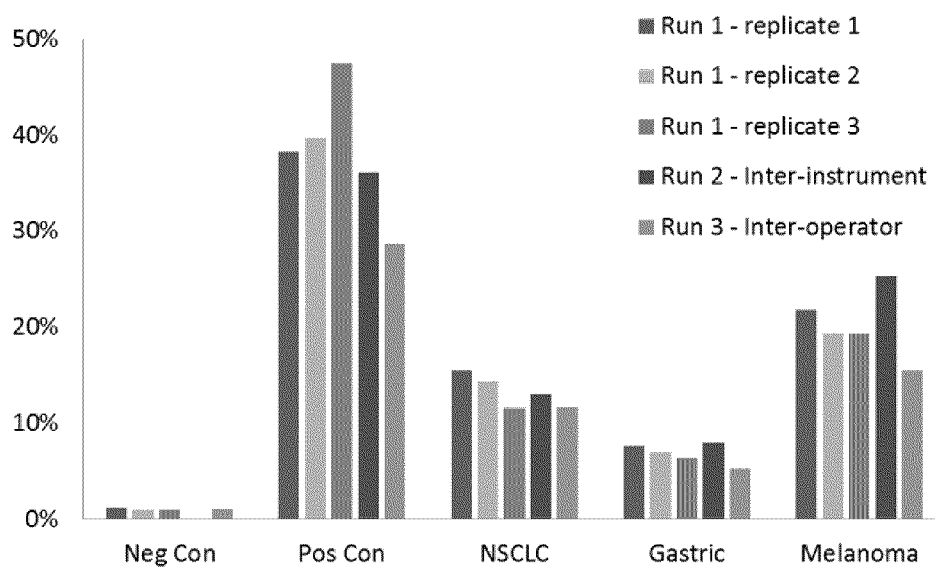
FIG. 23a shows a non-limiting example of quantitative assessment of CD4 on NSCLC, gastric, and melanoma tissues.
Figure 23B:
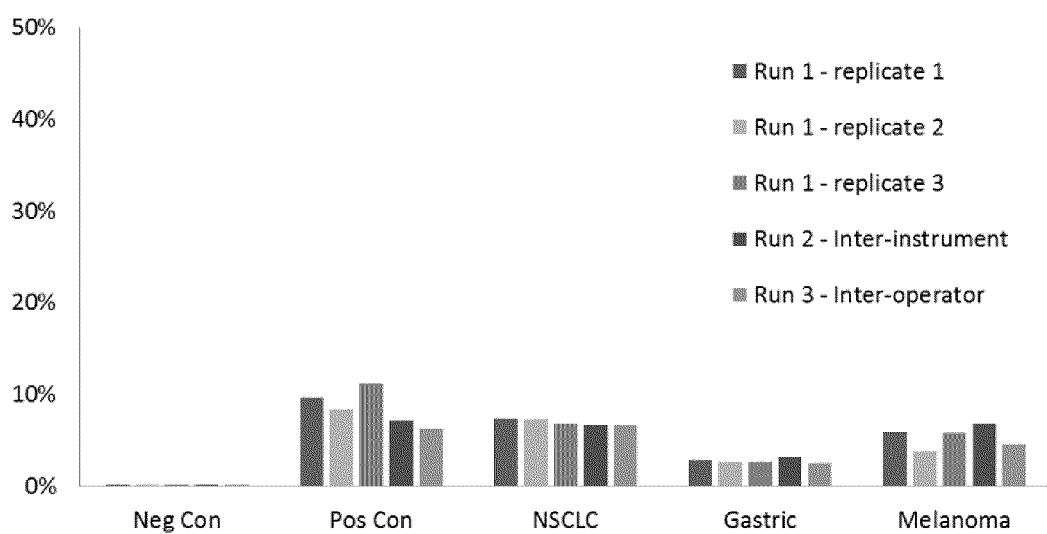
FIG. 23b shows a non-limiting example of quantitative assessment of CD8 on NSCLC, gastric, and melanoma tissues.

Analogous procedures as Example 16 were performed with the additional identification of tumor cells with either anti-S100 or anti-cytokeratin antibodies detected with an AlexaFluor488 secondary antibody and imaged across DAPI, FITC, Cy® 3, and Cy® 5 wavelengths for quantitative assessment of CD4 and CD8 on NSCLC, gastric, and melanoma tissues. The tissues were stained with antibodies recognizing CD4 and CD8 and their expressions in non-tumor areas were calculated as % expression. A broad range of expression (10%-50%) was observed for CD4+ and CD8+ T-cells in sequential sections of the tumor specimens. Results are shown in FIGS. 23a and 23b.

Example 20. Assessment of Myeloid Derived Suppressor Cell (MDSC)-Like Cells in Tumor Samples from Patients Diagnosed with Metastatic Melanoma or Non-Small Cell Lung Cancer To identify MDSC-like cells expressing phenotypic markers characteristic of myeloid cells (e.g., CD11b, CD33, and HLA-DR) and biochemical markers (e.g., ARG1 and IDO-1) that render suppressive function upon these cells, samples were stained with either CD11b, HLA-DR, and IDO, or CD11b, CD33, and ARG1.

Differential expression of CD11b, HLA-DR and IDO-1 was utilized to survey presence of a subset of suppressive myeloid cells known as TAMs (tumor associated macrophages) in tumor biopsies from metastatic melanoma patients. Representative sub-phenotypes that may be relevant for predicting response to cancer immunotherapies are shown in FIGS. 24a, 24b, 25a, and 25b.

Figure 26A:
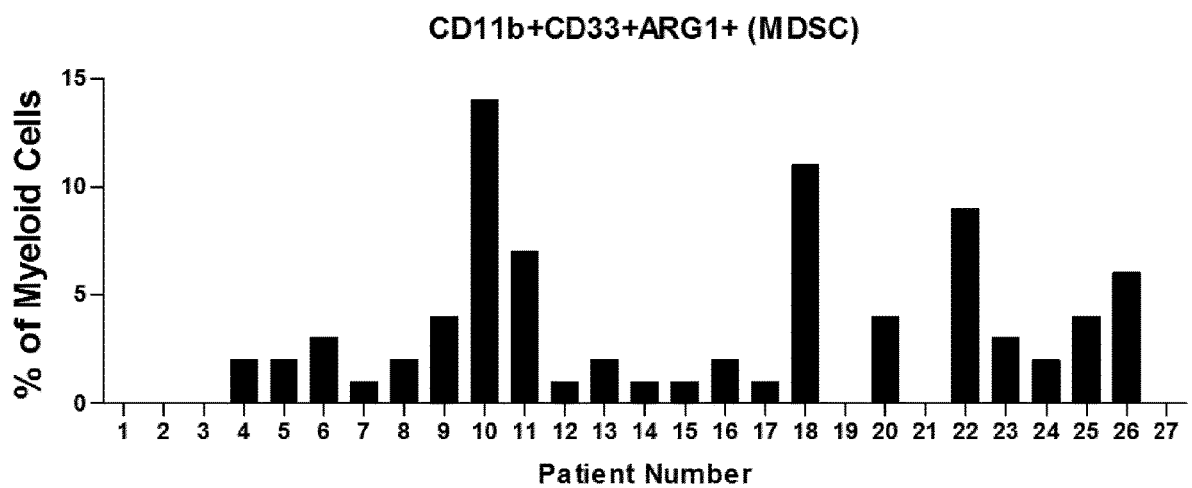
FIG. 26a shows a non-limiting example of quantitative assessment of CD11b+/CD33+/ARG1+ phenotype on NSCLC tissues.
Figure 26B:
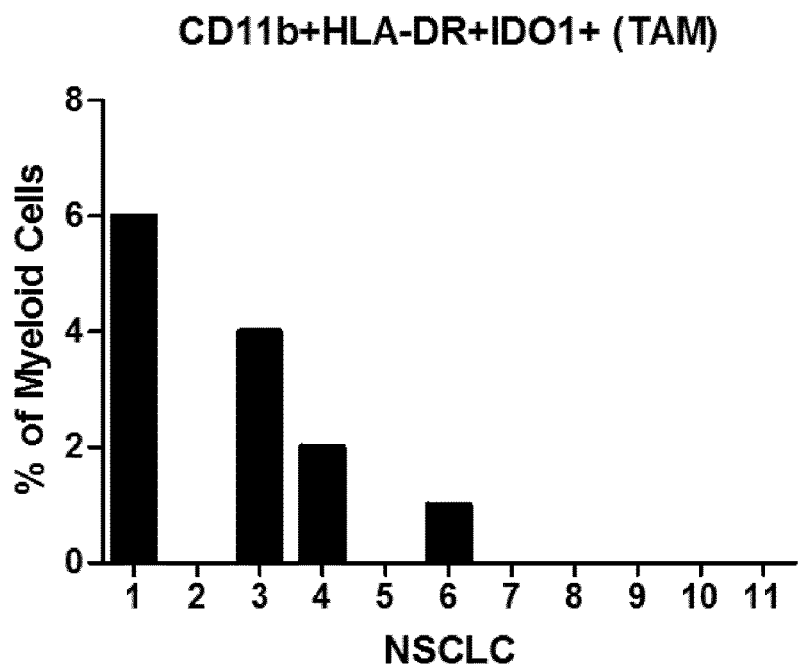
FIG. 26b shows a non-limiting example of quantitative assessment of CD11b+/HLA-DR+/IDO-1+ phenotype on NSCLC tissues.
Figure 27:
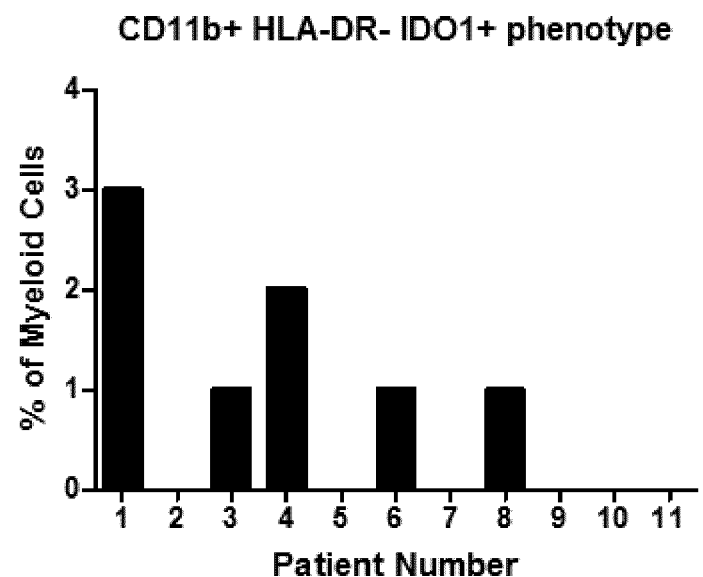
FIG. 27 shows a non-limiting example of quantitative assessment of CD11b+/HLA-DR−/IDO-1+ phenotype on NSCLC tissues.

Differential expression of CD11b, CD33, and ARG-1 or CD11b, HLA-DR, and IDO-1 were utilized to survey presence of MDSC like cells and TAMs in tumor specimens from advanced lung cancer (NSCLC) patients. Representative sub-phenotypes that may be relevant for predicting response to cancer immunotherapies are shown in FIGS. 26a, 26b, and 27.

Sample Preparation.

Formalin fixed paraffin embedded (FFPE) tissue samples were dewaxed. The slides were then rehydrated through a series of xylene to alcohol washes before incubating in distilled water. Heat-induced antigen retrieval was then performed using elevated pressure and temperature conditions, allowed to cool, and transferred to Tris-buffered saline. Staining was then performed where the following steps were carried out. First, endogenous peroxidase was blocked followed by incubation with a protein-blocking solution to reduce nonspecific antibody staining. Next, the slides were stained with either a rabbit anti-IDO-1 or mouse anti-CD33 primary antibody. Slides were then washed before incubation with anti-rabbit or anti-mouse HRP secondary antibody. Slides were washed and then anti-IDO-1 or anti-CD33 staining was detected using TSA+Cy® 5 (Perkin Elmer). Any residual HRP was then quenched using two washes of fresh 100 mM benzhydrazide with 50 mM hydrogen peroxide. The slides were again washed before staining with a mouse anti-HLA-DR or a rabbit anti-ARG1 primary antibody. Slides were washed and then incubated with anti-mouse or anti-rabbit HRP secondary antibody. Slides were washed and then the anti-HLA-DR or anti-ARG1 staining was detected using TSA-Cy® 3 (Perkin Elmer). Primary and secondary antibody reagents were then removed via microwave. The slides were again washed before staining with a rabbit anti-CD11b antibody. Slides were washed and then incubated with a cocktail of anti-rabbit HRP secondary antibody plus 4',6-diamidino-2-phenylindole (DAPI). Slides were washed and then anti-CD11b staining was detected using TSA-AlexaFluor488 (Life Technologies). Slides were washed a final time before they were cover-slipped with mounting media and allowed to dry overnight at room temperature.

Analogous procedures to Example 16 were used for sample imaging and analysis across DAPI, FITC, Cy® 3, and Cy®5 wavelengths. 4× magnification images were processed using an automated enrichment algorithm (developed using inForm) in field of view selector 104 to identify and rank possible 20× magnification fields of view according to the highest Cy® 3 and Cy® 5 expression.

Each DAPI image was processed by cell masker 212 to identify all cell nuclei within that image and then dilated to represent the approximate size of an entire cell. This resulting mask represented all cells within that images Each AlexaFluor488® image was processed by biomarker masker 222 to create a binary mask of all cells that are CD11b positive.

Each Cy® 3 image was processed by biomarker masker 222 to create a binary mask of all cells that are HLA-DR or CD33 positive.

Each Cy® 5 image was processed by biomarker masker 222 to create a binary mask of all cells that are IDO-1 or ARG1 positive.

The binary masks for all cells CD11b positive and HLA-DR positive were combined to create a binary mask of all cells that are either double positive for CD11b and HLA-DR or are CD11b positive and HLA-DR negative.

Figure 24A:
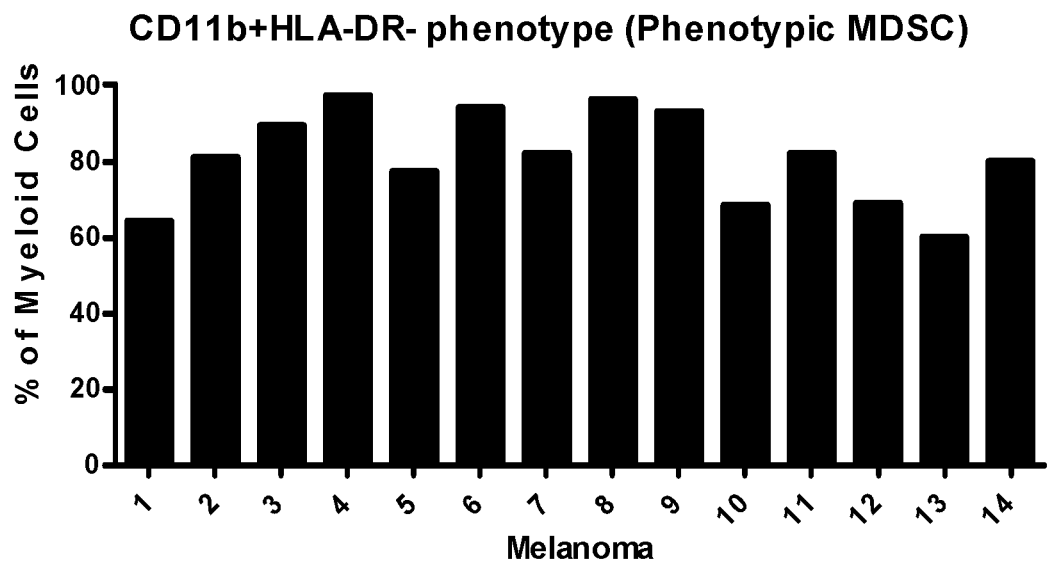
FIG. 24a shows a non-limiting example of quantitative assessment of CD11b+/HLA-DR− phenotype on metastatic melanoma tissues.

The % biomarker positivity (PBP) for all CD11b cells lacking expression of HLA-DR was derived, using positivity calculator 236, by dividing the total area, measured in pixels and determined by area evaluator 232, of the mask of all CD11b-positive, HLA-DR– negative cells with the total area, measured in pixels and determined by area evaluator 232, of the mask of all CD11b-positive cells. Results are shown in FIG. 24a for tumor samples obtained from patients diagnosed with metastatic melanoma.

The binary masks for all cells CD11b positive, IDO positive, and HLA-DR positive were combined to create a binary mask of all cells that are CD11b-positive, HLA-DR-negative, and IDO-1-positive.

Figure 24B:
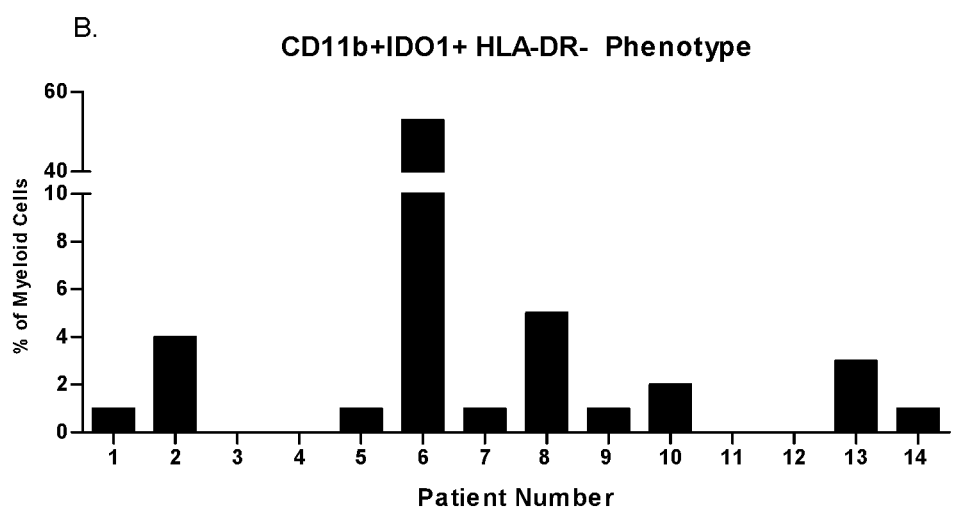
FIG. 24b shows a non-limiting example of quantitative assessment of CD11b+/IDO-1+/HLA-DR− phenotype on metastatic melanoma tissues.

The PBP for all CD11b cells expressing IDO-1, but lacking expression of HLA-DR was derived by dividing the total area, measured in pixels, of the mask of all CD11b-positive, HLA-DR-negative, IDO-1-positive cells with the total area, measured in pixels, of the mask of all CD11b-positive cells. Results are shown in FIG. 24b for tumor samples obtained from patients diagnosed with metastatic melanoma and FIG. 27 for patients diagnosed with non-small cell lung cancer.

The binary masks for all cells HLA-DR positive and IDO-1 positive were combined to create a binary mask of all cells that are double positive for HLA-DR and IDO-1.

Figure 25A:
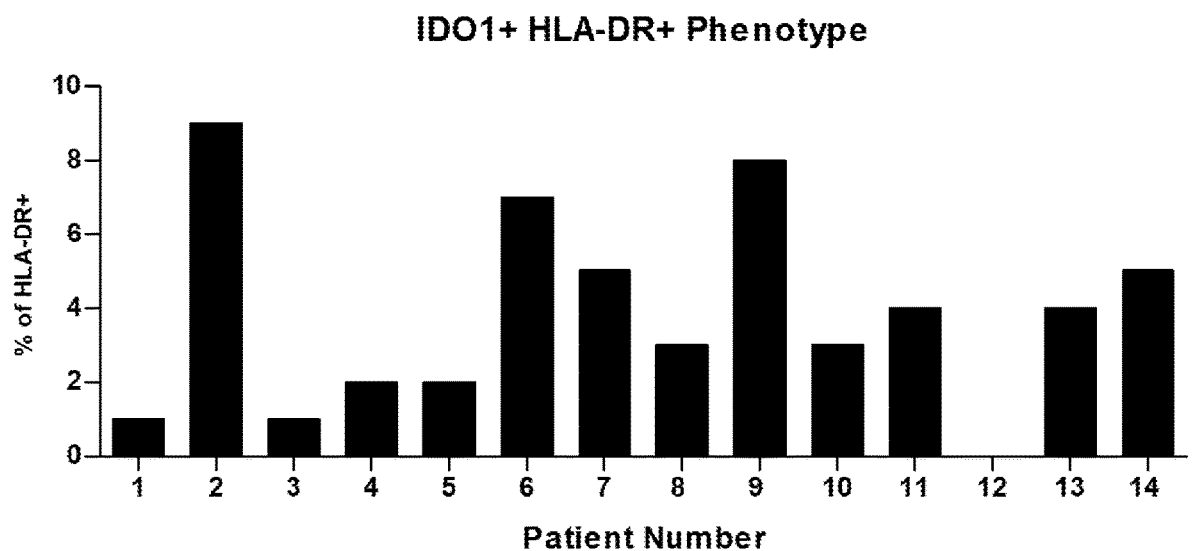
FIG. 25a shows a non-limiting example of quantitative assessment of IDO-1+/HLA-DR+ phenotype on metastatic melanoma tissues.

The % biomarker positivity (PBP) for all HLA-DR cells expressing IDO-1 was derived, using positivity calculator 236, by dividing the total area, measured in pixels and determined by area evaluator 232, of the mask of all IDO-1-positive, HLA-DR-positive cells with the total area, measured in pixels and determined by area evaluator 232, of the mask of all HLA-DR-positive cells. Results are shown in FIG. 25a for tumor samples obtained from patients diagnosed with metastatic melanoma.

The binary masks for all cells CD11b positive, IDO positive, and HLA-DR positive were combined to create a binary mask of all cells that are CD11b-positive, HLA-DR-positive, and IDO-1-positive.

Figure 25B:
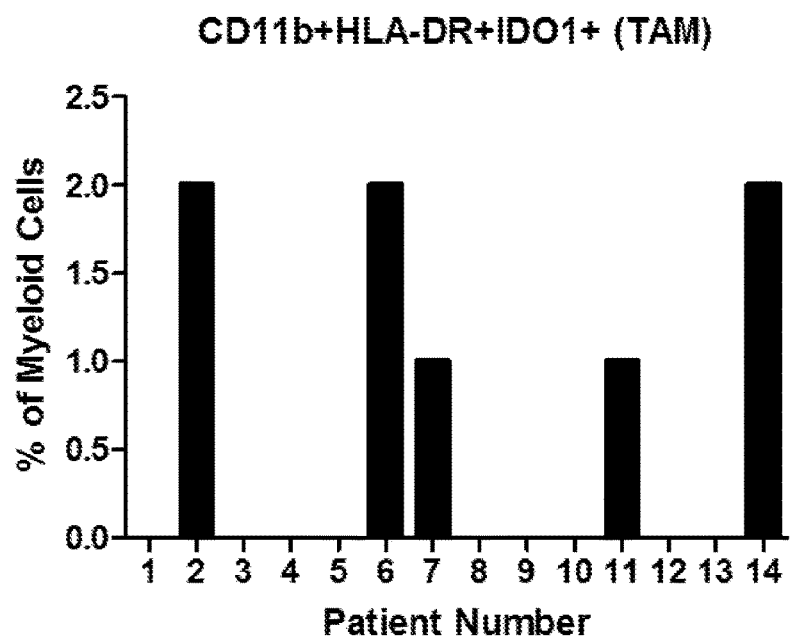
FIG. 25b shows a non-limiting example of quantitative assessment of CD11b+/IDO-1+/HLA-DR+ phenotype on metastatic melanoma tissues.

The PBP for all CD11b cells expressing IDO-1 and HLA-DR was derived by dividing the total area, measured in pixels, of the mask of all CD11b-positive, HLA-DR-positive, IDO-1-positive cells with the total area, measured in pixels, of the mask of all CD11b-positive cells. Results are shown in FIG. 25b for tumor samples obtained from patients diagnosed with metastatic melanoma and FIG. 26b for tumor samples obtained from patients diagnosed with non-small cell lung cancer.

The binary masks for all cells CD11b positive, CD33 positive, and ARG1 positive were combined to create a binary mask of all cells that are CD11b-positive, CD33-positive, and ARG1-positive.

The PBP for all CD11b cells expressing CD33 and ARG1 was derived by dividing the total area, measured in pixels, of the mask of all CD11b-positive, CD33-positive, ARG1-positive cells with the total area, measured in pixels, of the mask of all CD11b-positive cells. Results are shown in FIG. 26a for tumor samples obtained from patients diagnosed with non-small cell lung cancer.

Figure 28:
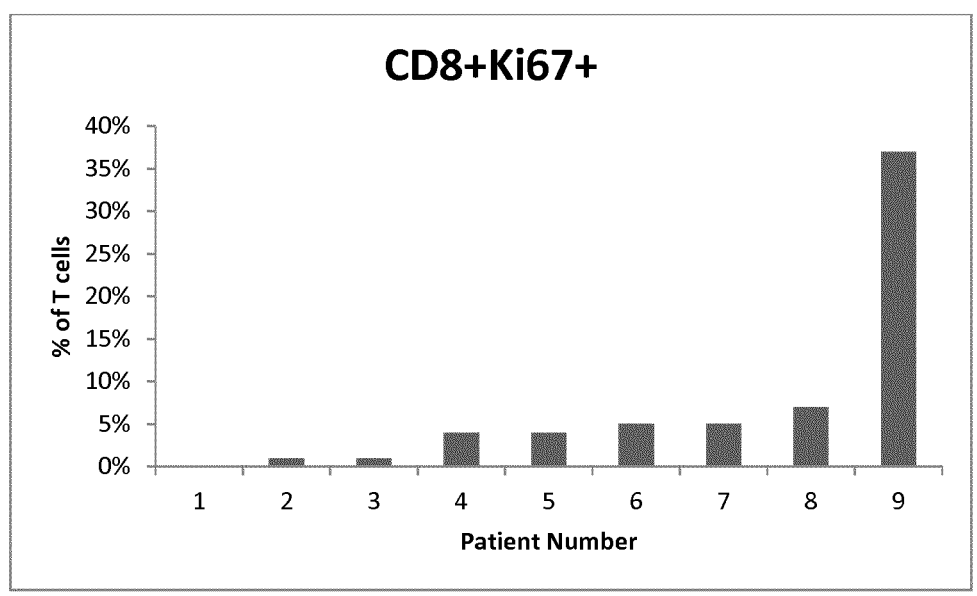
FIG. 28 shows a non-limiting example of quantitative assessment of CD8+Ki67+ T cells on metastatic melanoma tissues.

Example 21. Assessment of Activated T Cells in Tumor Samples from Patients Diagnosed with Metastatic Melanoma Analogous procedures as Example 20 were performed to stain each sample with a combination of DAPI, CD3, CD8, and Ki67 to identify sub-populations of activated T cells. Prevalence of CD8+Ki67+ was surveyed in tumor biopsies obtained from patients diagnosed with metastatic melanoma (FIG. 28).

Figure 29A:
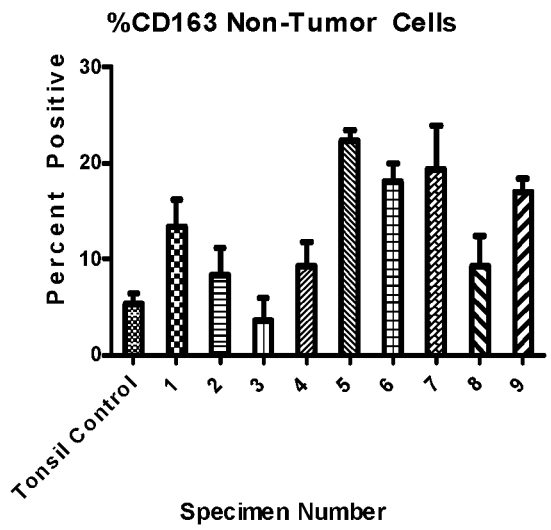
FIG. 29a shows a non-limiting example of quantitative assessment of CD163+ cells on metastatic melanoma tissues.
Figure 29B:
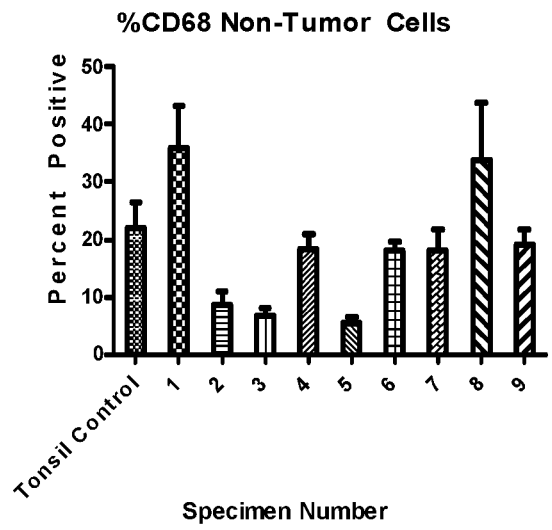
FIG. 29b shows a non-limiting example of quantitative assessment of CD68+ cells on metastatic melanoma tissues.
Figure 29C:
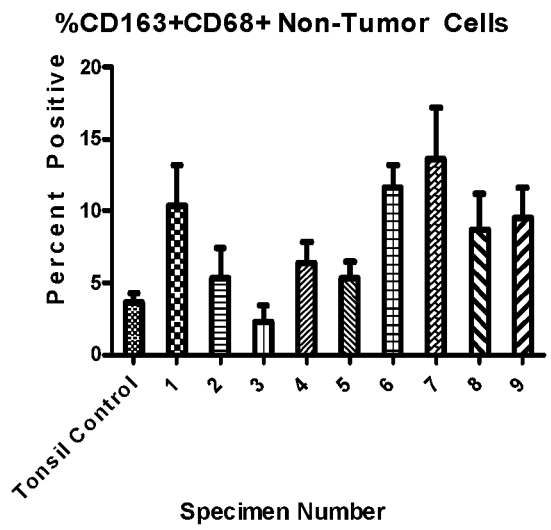
FIG. 29c shows a non-limiting example of quantitative assessment of CD163+CD68+ cells on metastatic melanoma tissues.

Example 22. Assessment of Macrophage Prevalence in Tumor Samples from Patients Diagnosed with Metastatic Melanoma Analogous procedures as Example 16 were performed with the additional identification of tumor cells with anti-S100 antibody detected with an AlexaFluor488 secondary antibody and imaged across DAPI, FITC, Cy® 3, and Cy® 5 wavelengths for quantitative assessment of CD163 and CD68 on melanoma tissues. The tissues were stained with antibodies recognizing CD163 and CD68 and their expression in non-tumor areas were calculated as single PBP expression or double PBP expression. Results are shown in FIGS. 29a, 29b, and 29c.

Example 23. Assessment of T Cell Suppression Prevalence in Tumor Samples from Patients Diagnosed with Diffuse Large B-Cell Lymphoma (DLBCL) and Neuroendocrine Tumors (NET)

Figure 30A:
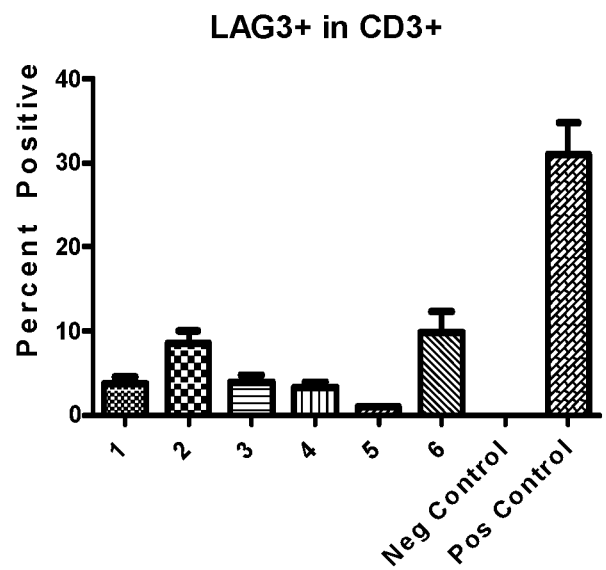
FIG. 30a shows a non-limiting example of quantitative assessment of LAG-3 positive T cells on DLBCL and NET tissues.
Figure 30B:
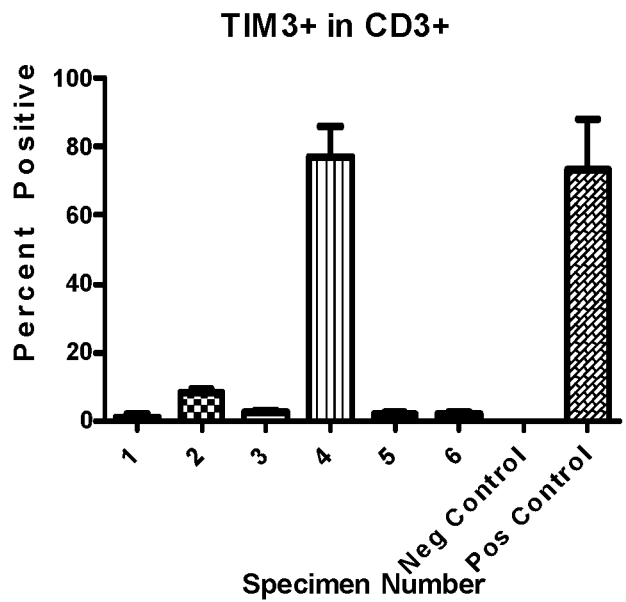
FIG. 30b shows a non-limiting example of quantitative assessment of TIM-3 positive T cells on DLBCL and NET tissues.

Analogous procedures as Example 1 were performed to stain the DLBCL and NET tumor specimens with a mouse anti-LAG-3 primary antibody, anti-mouse HRP secondary, detected with TSA+Cy® 3.5, with remaining HRP quenched with 100 mM benzhydrazide and 50 mM hydrogen peroxide. Following this, slides were stained with a rabbit anti-TIM-3 primary antibody, anti-rabbit HRP secondary, detected with TSA-Cy® 5. Primary and secondary antibodies were then removed via microwave. Tissues were then stained with a rabbit anti-CD3 primary antibody, anti-rabbit HRP secondary plus 4',6-diamidino-2-phenylindole (DAPI), detected with Opal™ 520. Imaging was performed analogous to Example 1 across DAPI, FITC, Texas Red, and Cy® 5 wavelengths. Analysis was performed analogous to Example 1 to determine PBP prevalence of T cells that were LAG-3 and TIM-3 positive respectively. Results are shown in FIGS. 30a and 30b.

Para. A. A method of deriving a value for % biomarker positivity (PBP) for all cells or, optionally, one or more subsets thereof present in a field of view, comprising:
  (i) generating an image of first fluorescence signals representative of nuclei of all cells present in a field of view, and dilating the first fluorescence signals to a diameter of that of an entire cell to construct a first mask of all cells present in the field of view;
  (ii) constructing a second mask of second fluorescence signals representative of all areas present in the field of view, which express a subset biomarker;
  (iii) optionally, constructing a third mask of third fluorescence signals representative of all areas present in the field of view, which express a first biomarker of interest;
  (iv) combining said first and second masks in a manner that provides a fourth mask comprising fluorescence signals representative of all cells in the field of view, which also express the subset biomarker;
  (v) optionally, combining said first and third masks in a manner that provides a fifth mask comprising fluorescence signals representative of a first subset of all cells in the field of view, which also express the first biomarker of interest;
  (vi) deriving a value for PBP for all cells expressing the subset biomarker by dividing the total area of the fourth mask by the total area of the first mask;
  (vii) optionally, combining said fourth and fifth masks in a manner that provides a sixth mask comprising fluorescence signals representative of the first subset of all cells in the field of view, which express the subset biomarker and the first biomarker of interest; and
  (viii) optionally, deriving a value for PBP for the first subset of all cells expressing the subset biomarker and the first biomarker of interest by dividing the total area of the sixth mask by the total area of the fourth mask.

Para. B. The method of Para. A in which all the recited optional steps are performed.

Para. C. The method of Para. A or Para. B which further comprises:
  (ix) constructing a seventh mask of fourth fluorescence signals representative of all areas present in the field of view, which express a second biomarker of interest;
  (x) combining said first and seventh masks in a manner that provides an eighth mask comprising fluorescence signals representative of a second subset of all cells in the field of view, which also express the second biomarker of interest;
  (xi) combining said fourth and eighth masks in a manner that provides a ninth mask comprising fluorescence signals representative of the second subset of all cells in the field of view, which express the subset biomarker and the second biomarker of interest; and
  (xii) deriving a value for PBP for the second subset of all cells expressing the subset biomarker and the second biomarker of interest by dividing the total area of the ninth mask by the total area of the fourth mask.

Para. D. The method of Para. A or Para. B which further comprises:
  (ix) constructing a seventh mask of fourth fluorescence signals representative of all areas present in the field of view, which express a second biomarker of interest;
  (x) subtracting said second mask from said first mask in a manner that provides an eighth mask comprising fluorescence signals representative of all cells that do not express the subset biomarker in the field of view;

(xi) combining said seventh and eighth masks in a manner that provides a ninth mask comprising fluorescence signals representative of all cells that express the second biomarker of interest but do not express the subset biomarker in the field of view; and (xii) deriving a value for PBP for all cells that express the second biomarker of interest but do not express the subset biomarker by dividing the total area of the ninth mask by the total area of the eighth mask.

Para. E. The method of any one of Paras. A-D in which the first biomarker of interest comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. F. The method of any one of Paras. A-D in which the first biomarker of interest comprises a biomarker selected from PD-L1, Galectin 9, and MHC.

Para. G. The method of Para. D in which the second biomarker of interest comprises a biomarker selected from PD-1, TIM-3, and TCR.

Para. H. The method of Para. D in which the second biomarker of interest is different from the first biomarker of interest and comprises a biomarker selected from PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. I. The method of any one of Paras. A-E in which the first subset of all the cells in the field of view comprises tumor cells.

Para. J. The method of any one of Paras. A-D in which the first subset of all the cells in the field of view comprises non-tumor cells.

Para. K. The method of Para. J in which the first subset of all the cells in the field of view comprises T-cells.

Para. L. The method of Para. K in which the T-cells express CD3.

Para. M. The method of Para. K in which the T-cells express CD8.

Para. N. The method of Para. K in which the T-cells express CD4.

Para. O. The method of any one of Paras. A-D in which the subset biomarker is expressed only in tumor cells.

Para. P. The method of any one of Paras. A-D in which the subset biomarker is expressed only in non-tumor cells.

Para. Q. The method of any one of Paras. A-D in which the subset biomarker is expressed in T-cells.

Para. R. The method of any one of Paras. A-D in which the subset biomarker comprises CD3.

Para. S. The method of any one of Paras. A-D in which the subset biomarker comprises CD19.

Para. T. The method of Para. B in which the first biomarker of interest comprises Ki67 and said first subset of all the cells in the field of view comprises CD8 positive cells.

Para. U. The method of any one of Paras. A-T in which the total area is measured in pixels.

Para. V. A method of monitoring a progress of a patient diagnosed with cancer and undergoing immunotherapy, comprising:

(i) using at least two samples comprising tumor tissue taken from a cancer patient over at least two time points, one prior to and one after initiation of immunotherapy, deriving a value for % biomarker positivity (PBP) for all non-tumor cells expressing a biomarker of interest for each of said at least two samples to obtain at least a first value for PBP and at least a second value for PBP;

(ii) recording said at least first value for PBP and said at least second value for PBP, a change between said at least first value for PBP and said at least second value for PBP being indicative of an effectiveness of said immunotherapy.

Para. W. The method of Para. V in which the change is a decrease between said at least first value for PBP and said at least second value for PBP, the decrease being indicative of a positive effectiveness of said immunotherapy.

Para. X. The method of Para. V in which the change is an increase between said at least first value for PBP and said at least second value for PBP, the increase being indicative of a positive effectiveness of said immunotherapy.

Para. Y. The method of any one of Paras. V-X in which said immunotherapy comprises immune checkpoint therapy.

Para. Z. A method of monitoring a progress of a patient diagnosed with cancer and undergoing immunotherapy, comprising:

(i) using at least two samples comprising tumor tissue taken from a cancer patient over at least two time points, one prior to and one after initiation of immunotherapy, deriving a value for % biomarker positivity (PBP) for all tumor cells expressing a biomarker of interest for each of said at least two samples to obtain at least a first value for PBP and at least a second value for PBP;

(ii) recording said at least first value for PBP and said at least second value for PBP, a change between said at least first value for PBP and said at least second value for PBP being indicative of an effectiveness of said immunotherapy.

Para. AA. The method of Para. Z in which the change is a decrease between said at least first value for PBP and said at least second value for PBP, the decrease being indicative of a positive effectiveness of said immunotherapy.

Para. AB. The method of Para. Z in which the change is an increase between said at least first value for PBP and said at least second value for PBP, the increase being indicative of a positive effectiveness of said immunotherapy.

Para. AC. The method of any one of Paras. Z-AB in which said immunotherapy comprises immune checkpoint therapy.

Para. AD. A method of deriving a value for % biomarker positivity (PBP) for all tumor cells present in a field of view, comprising:

(i) generating an image of first fluorescence signals representative of nuclei of all cells present in a field of view, and dilating the first fluorescence signals to a diameter of that of an entire cell to construct a first mask of all cells present in the field of view;

(ii) constructing a second mask of second fluorescence signals representative of all areas present in the field of view, which express a tumor biomarker;

(iii) combining said first and second masks in a manner that provides a third mask comprising fluorescence signals representative of all tumor cells in the field of view;

(iv) constructing a fourth mask of third fluorescence signals representative of all areas present in the field of view, which express a biomarker of interest;

(v) combining said third and fourth masks in a manner that provides a fifth mask comprising fluorescence signals representative of all tumor cells in the field of view, which also express the biomarker of interest; and (vi) deriving a value for PBP for all tumor cells expressing the biomarker of interest by dividing the total area of the fifth mask by the total area of the third mask.

Para. AE. The method of Para. AD in which the biomarker of interest comprises a biomarker selected from the group consisting of PD-L1, Galectin 9, and MHC.

Para. AF. The method of Para. AD in which the field of view further comprises non-tumor cells.

Para. AG. The method of Para. AF in which the non-tumor cells comprise immune cells and stromal cells.

Para. AH. The method of any one of Paras. AD-AG in which the total area is measured in pixels.

Para. AI. A method of deriving a value for % biomarker positivity (PBP) for all non-tumor cells present in a field of view, comprising:
 (i) generating an image of first fluorescence signals representative of nuclei of all cells present in a field of view, and dilating the first fluorescence signals to a diameter of that of an entire cell to construct a first mask of all cells present in the field of view;
 (ii) constructing a second mask of second fluorescence signals representative of all areas present in the field of view, which express a tumor biomarker;
 (iii) subtracting said second mask from said first mask in a manner that provides a third mask comprising fluorescence signals representative of all non-tumor cells in the field of view;
 (iv) constructing a fourth mask of fluorescence signals representative of all areas present in the field of view, which express a biomarker of interest;
 (v) combining said third and fourth masks in a manner that provides a fifth mask comprising fluorescence signals representative of all non-tumor cells in the field of view, which also express the biomarker of interest;
 (vi) deriving a value for PBP for all non-tumor cells expressing the biomarker of interest by dividing the total area of the fifth mask by the total area of the third mask.

Para. AJ. The method of Para. AI in which the biomarker of interest comprises a biomarker selected from the group consisting of PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. AK. The method of Para. AI in which the biomarker of interest comprises a biomarker selected from the group consisting of CD11b, CD33, HLA-DR, IDO-1, ARG1, granzyme B, B2M, PD-L1, PD-L2, B7-H3, B7-H4, HLA-DR, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. AL. The method of Para. AI in which the non-tumor cells comprise immune cells and stromal cells.

Para. AM. The method of Para. AI in which the non-tumor cells comprise myeloid cells.

Para. AN. A method of deriving a value for % biomarker positivity (PBP) for all cells or, optionally, one or more subsets thereof present in a field of view, comprising:
 (i) generating an image of first fluorescence signals representative of nuclei of all cells present in a field of view, and dilating the first fluorescence signals to a diameter of that of an entire cell to construct a first mask of all cells present in the field of view;
 (ii) constructing a second mask of second fluorescence signals representative of all areas present in the field of view, which express a subset biomarker;
 (iii) optionally, constructing a third mask of third fluorescence signals representative of all areas present in the field of view, which express a first biomarker of interest;
 (iv) combining said first and second masks in a manner that provides a fourth mask comprising fluorescence signals representative of all cells in the field of view, which also express the subset biomarker;
 (v) optionally, combining said first and third masks in a manner that provides a fifth mask comprising fluorescence signals representative of all cells in the field of view, which also express the first biomarker of interest;
 (vi) deriving a value for PBP for all cells expressing the subset biomarker by dividing the total area of the fourth mask by the total area of the first mask;
 (vii) optionally, combining said fourth and fifth masks in a manner that provides a sixth mask comprising fluorescence signals representative of all cells in the field of view, which
  (a) express the subset biomarker and the first biomarker of interest; or
  (b) express the subset biomarker in the absence of the first biomarker of interest; and
 (viii) optionally, deriving a value for PBP for the first subset of all cells which either (a) express the subset biomarker and the first biomarker of interest or (b) express the subset biomarker in the absence of the first biomarker of interest, by dividing the total area of the sixth mask by the total area of the fourth mask.

Para. AO. The method of Para. AN in which all the recited optional steps are performed.

Para. AP. The method of Para. AN or Para. AO which further comprises:
 (ix) constructing a seventh mask of fourth fluorescence signals representative of all areas present in the field of view, which express a second biomarker of interest;
 (x) combining said first and seventh masks in a manner that provides an eighth mask comprising fluorescence signals representative of a second subset of all cells in the field of view, which also express the second biomarker of interest;
 (xi) combining said fourth and eighth masks in a manner that provides a ninth mask comprising fluorescence signals representative of the second subset of all cells in the field of view, which express the subset biomarker and the second biomarker of interest; and
 (xii) deriving a value for PBP for the second subset of all cells expressing the subset biomarker and the second biomarker of interest by dividing the total area of the ninth mask by the total area of the fourth mask.

Para. AQ. The method of Para. AN or Para. AO which further comprises:
 (ix) constructing a seventh mask of fourth fluorescence signals representative of all areas present in the field of view, which express a second biomarker of interest;
 (x) subtracting said second mask from said first mask in a manner that provides an eighth mask comprising fluorescence signals representative of all cells that do not express the subset biomarker in the field of view;
 (xi) combining said seventh and eighth masks in a manner that provides a ninth mask comprising fluorescence signals representative of all cells that express the second biomarker of interest but do not express the subset biomarker in the field of view;

and
(xii) deriving a value for PBP for all cells that express the second biomarker of interest but do not express the subset biomarker by dividing the total area of the ninth mask by the total area of the eighth mask.

Para. AR. The method of Para. AN which further comprises:
(ix) constructing a seventh mask of fourth fluorescence signals representative of all areas present in the field of view, which express a second biomarker of interest;
(x) combining said sixth and seventh masks in a manner that provides an eighth mask comprising fluorescence signals representative of all cells that
  (a) express the subset biomarker, the first biomarker of interest, and the second biomarker of interest in the field of view;
  (b) express the subset biomarker and the first biomarker of interest in the absence of the second biomarker of interest in the field of view; or
  (c) express the subset biomarker and the second biomarker of interest in the absence of the first biomarker of interest in the field of view;
and
(xii) deriving a value for PBP for all cells that express the first biomarker of interest or the second biomarker of interest, or a combination thereof, as well as the subset biomarker, by dividing the total area of the eighth mask by the total area of the fourth mask.

Para. AS. The method of any one of Paras. AN-AR in which the first biomarker of interest comprises a biomarker selected from CD11b, CD33, HLA-DR, IDO-1, ARG1, granzyme B, B2M, PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. AT. The method of any one of Paras. AN-AQ in which the first biomarker of interest comprises a biomarker selected from PD-L1, Galectin 9, and MHC.

Para. AU. The method of Para. AQ in which the second biomarker of interest comprises a biomarker selected from PD-1, TIM-3, and TCR.

Para. AV. The method of Para. AQ in which the second biomarker of interest is different from the first biomarker of interest and comprises a biomarker selected from CD11b, CD33, HLA-DR, IDO-1, ARG1, granzyme B, B2M, PD-L1, PD-L2, B7-H3, B7-H4, HLA-DR, Galectin 9, CD80, CD86, 4.1BBL, ICOSL, CD40, OX40L, IDO-1, GITRL, PD-1, TIM3, LAG3, 41BB, OX40, CTLA-4, CD40L, CD28, GITR, ICOS, CD28, CD3, CD4, CD8, FoxP3, CD25, CD16, CD56, CD68, CD163, CD80, and CD86.

Para. AW. The method of any one of Paras. AN-AR in which the first subset of all the cells in the field of view comprises tumor cells.

Para. AX. The method of any one of Paras. AN-AR in which the first subset of all the cells in the field of view comprises non-tumor cells.

Para. AY. The method of Para. AX in which the first subset of all the cells in the field of view comprises T-cells.

Para. AZ. The method of Para. AY in which the T-cells express CD3.

Para. BA. The method of Para. AY in which the T-cells express CD8.

Para. BB. The method of Para. AY in which the T-cells express CD4.

Para. BC. The method of Para AX in which the first subset of all the cells in the field of view comprises myeloid cells.

Para. BD. The method of Para. BC in which the myeloid cells are myeloid derived suppressor cells.

Para. BE. The method of Para. BC in which the myeloid cells are tumor associated macrophages.

Para. BF. The method of any one of Paras. AN-AR in which the subset biomarker is expressed only in tumor cells.

Para. BG. The method of any one of Paras. AN-AR in which the subset biomarker is expressed only in non-tumor cells.

Para. BH. The method of any one of Paras. AN-AR in which the subset biomarker is expressed in T-cells.

Para. BI. The method of any one of Paras. AN-AR in which the subset biomarker comprises CD3.

Para. BJ. The method of any one of Paras. AN-AR in which the subset biomarker comprises CD19.

Para. BK. The method of any one of Paras. AN-AR in which the subset biomarker is expressed in myeloid cells.

Para. BL. The method of any one of Paras. AN-AR in which the subset biomarker is expressed in myeloid derived suppressor cells.

Para. BM. The method of any one of Paras. AN-AR in which the subset biomarker is expressed in tumor associated macrophages.

Para. BN. The method of Para. AO in which the first biomarker of interest comprises Ki67 and said first subset of all the cells in the field of view comprises CD8 positive cells.

Para. BO. The method of any one of Paras. AN-BN in which the total area is measured in pixels.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A method of deriving a value for % biomarker positivity (PBP) for all cells or, optionally, one or more subsets thereof present in a field of view, comprising:
   (i) generating an image of first fluorescence signals representative of nuclei of all cells present in a field of view, consisting of
      (a) obtaining pixel data of fluorescence emission from nuclei of all cells present in a field of view, which are stained with a fluorophore;
      (b) evaluating each pixel observed for its pixel intensity value and resetting this value to zero if this value falls below a user-defined lower bound;
      (c) compiling a histogram distribution of non-zero pixel intensity values; and
      (d) resetting the non-zero pixel intensity values above a user-defined histogram threshold to 1 to arrive at the image of first fluorescence signals representative of nuclei of all cells present in the field of view;
   and dilating the image of the first fluorescence signals to a diameter of that of an entire cell to construct a first mask of all cells present in the field of view;
   (ii) constructing a second mask of second fluorescence signals representative of all areas present in the field of view, which express a subset biomarker;
   (iii) optionally, constructing a third mask of third fluorescence signals representative of all areas present in the field of view, which express a first biomarker of interest;
   (iv) combining said first and second masks in a manner that provides a fourth mask comprising fluorescence signals representative of all cells in the field of view, which also express the subset biomarker;
   (v) optionally, combining said first and third masks in a manner that provides a fifth mask comprising fluorescence signals representative of all cells in the field of view, which also express the first biomarker of interest;
   (vi) deriving a value for PBP for all cells expressing the subset biomarker by dividing the total area of the fourth mask by the total area of the first mask;
   (vii) optionally, combining said fourth and fifth masks in a manner that provides a sixth mask comprising fluorescence signals representative of all cells in the field of view, which
      (a) express the subset biomarker and the first biomarker of interest; or
      (b) express the subset biomarker in the absence of the first biomarker of interest; and
   (viii) optionally, deriving a value for PBP for a first subset of all cells which either (a) express the subset biomarker and the first biomarker of interest or (b) express the subset biomarker in the absence of the first biomarker of interest, by dividing the total area of the sixth mask by the total area of the fourth mask.

2. The method of claim 1 in which all the recited optional steps are performed.

3. The method of claim 1 which further comprises:
   (ix) constructing a seventh mask of fourth fluorescence signals representative of all areas present in the field of view, which express a second biomarker of interest;
   (x) combining said first and seventh masks in a manner that provides an eighth mask comprising fluorescence signals representative of all cells in the field of view, which also express the second biomarker of interest;
   (xi) combining said fourth and eighth masks in a manner that provides a ninth mask comprising fluorescence signals representative of all cells in the field of view, which express the subset biomarker and the second biomarker of interest; and
   (xii) deriving a value for PBP for a second subset of all cells expressing the subset biomarker and the second biomarker of interest by dividing the total area of the ninth mask by the total area of the fourth mask.

4. The method of claim 1 which further comprises:
   (ix) constructing a seventh mask of fourth fluorescence signals representative of all areas present in the field of view, which express a second biomarker of interest;
   (x) subtracting said second mask from said first mask in a manner that provides an eighth mask comprising fluorescence signals representative of all cells that do not express the subset biomarker in the field of view;
   (xi) combining said seventh and eighth masks in a manner that provides a ninth mask comprising fluorescence signals representative of all cells that express the second biomarker of interest but do not express the subset biomarker in the field of view; and
   (xii) deriving a value for PBP for all cells that express the second biomarker of interest but do not express the subset biomarker by dividing the total area of the ninth mask by the total area of the eighth mask.

5. The method of claim 4 in which the second biomarker of interest is different from the first biomarker of interest and comprises a biomarker selected from CD11b, CD33, HLA-DR, IDO-1, ARG1, granzyme B, B2M, PD-L1, PD-L2, B7-H3, B7-H4, Galectin 9, 4-1BBL, ICOSL, CD40, OX40L, GITRL, PD-1, TIM3, LAG3, 4-1BB, OX40, CTLA-4, CD40L, CD28, GITR, ICOS, CD3, CD4, CD8, FoxP3, CD25, CD16, CD56, CD68, CD163, CD80, and CD86.

6. The method of claim 1 which further comprises:

(ix) constructing a seventh mask of fourth fluorescence signals representative of all areas present in the field of view, which express a second biomarker of interest;

(x) combining said sixth and seventh masks in a manner that provides an eighth mask comprising fluorescence signals representative of all cells that (a) express the subset biomarker, the first biomarker of interest, and the second biomarker of interest in the field of view;

(b) express the subset biomarker and the first biomarker of interest in the absence of the second biomarker of interest in the field of view; or (c) express the subset biomarker and the second biomarker of interest in the absence of the first biomarker of interest in the field of view; and (xii) deriving a value for PBP for all cells that express the first biomarker of interest or the second biomarker of interest, or a combination thereof, as well as the subset biomarker, by dividing the total area of the eighth mask by the total area of the fourth mask.

7. The method of claim 1 in which the first biomarker of interest comprises a biomarker selected from CD11b, CD33, HLA-DR, IDO-1, ARG1, granzyme B, B2M, PD-L1, PD-L2, B7-H3, B7-H4, Galectin 9, 4-1BBL, ICOSL, CD40, OX40L, GITRL, PD-1, TIM3, LAG3, 4-1BB, OX40, CTLA-4, CD40L, GITR, ICOS, CD28, CD3, CD4, CD8, FoxP3, CD25, CD16, CD56, CD68, CD163, CD80, and CD86.

8. The method of claim 1 in which the first subset of all the cells in the field of view comprises tumor cells.

9. The method of claim 1 in which the first subset of all the cells in the field of view comprises non-tumor cells.

10. The method of claim 9 in which the first subset of all the cells in the field of view comprises T-cells.

11. The method of claim 10 in which the T-cells express CD3, CD8, or CD4.

12. The method of claim 9 in which the first subset of all the cells in the field of view comprises myeloid cells.

13. The method of claim 12 in which the myeloid cells are myeloid derived suppressor cells or tumor associated macrophages.

14. The method of claim 1 in which the subset biomarker is expressed only in tumor cells.

15. The method of claim 1 in which the subset biomarker is expressed only in non-tumor cells.

16. The method of claim 1 in which the subset biomarker is expressed in T-cells.

17. The method of claim 1 in which the subset biomarker comprises CD3 or CD19.

18. The method of claim 1 in which the subset biomarker is expressed in myeloid cells, myeloid derived suppressor cells, or tumor associated macrophages.

* * * * *